(12) United States Patent
Yang et al.

(10) Patent No.: US 11,014,230 B2
(45) Date of Patent: May 25, 2021

(54) ACTUATORS

(71) Applicant: President and Fellows of Harvard College, Cambridge, MA (US)

(72) Inventors: Dian Yang, Cambridge, MA (US); George M. Whitesides, Newton, MA (US)

(73) Assignee: President and Fellows of Harvard College, Cambridge, MA (US)

(*) Notice: Subject to any disclaimer, the term of this patent is extended or adjusted under 35 U.S.C. 154(b) by 327 days.

(21) Appl. No.: 15/770,565

(22) PCT Filed: Nov. 9, 2016

(86) PCT No.: PCT/US2016/061078
§ 371 (c)(1),
(2) Date: Apr. 24, 2018

(87) PCT Pub. No.: WO2017/083350
PCT Pub. Date: May 18, 2017

(65) Prior Publication Data
US 2020/0238509 A1   Jul. 30, 2020

Related U.S. Application Data

(60) Provisional application No. 62/254,461, filed on Nov. 12, 2015.

(51) Int. Cl.
*B25J 9/14* (2006.01)
*B25J 9/10* (2006.01)
(Continued)

(52) U.S. Cl.
CPC ............. *B25J 9/142* (2013.01); *B25J 9/1075* (2013.01); *A61F 2002/5066* (2013.01);
(Continued)

(58) Field of Classification Search
CPC .......... B25J 9/142; B25J 9/1075; B25J 11/00; F15B 15/103; F15B 15/10
See application file for complete search history.

(56) References Cited

U.S. PATENT DOCUMENTS

| 2003/0159219 A1 | 8/2003 | Harrison et al. |
| 2007/0186712 A1 | 8/2007 | Ferraresi et al. |
(Continued)

FOREIGN PATENT DOCUMENTS

| WO | WO-2015/143281 A1 | 9/2015 |
| WO | WO-2016/011345 A1 | 1/2016 |

OTHER PUBLICATIONS

International Search Report and Written Opinion dated Jan. 9, 2017, in the International Application No. PCT/US2016/061078, 13 pages.

*Primary Examiner* — Abiy Teka
(74) *Attorney, Agent, or Firm* — Wilmer Cutler Pickering Hale and Dorr LLP

(57) ABSTRACT

A shear force actuator is described, including: two substantially parallel first structural components disposed along a first axis; a plurality of substantially parallel second structural components disposed between and bridging the two first structural components; a plurality of joint sections each joining the second structural component with the first structural components at an oblique angle of between 0 and 90 degrees to define a plurality of cells, each capable of being connected with a fluid inflation or deflation source; an elastic surface covering the remaining surfaces of the cells in a fluid-tight manner, wherein at least one of the joint section, the first structural components, and the second structural components is elastic so that cell collapses upon removal of fluid from the cell to generate a linear force along the first axis.

29 Claims, 25 Drawing Sheets

(51) Int. Cl.
 *A61F 2/50* (2006.01)
 *A61F 2/70* (2006.01)
 *B25J 11/00* (2006.01)
 *F15B 15/10* (2006.01)

(52) U.S. Cl.
 CPC .......... *A61F 2002/701* (2013.01); *B25J 11/00* (2013.01); *F15B 15/103* (2013.01)

(56) References Cited

U.S. PATENT DOCUMENTS

| | | |
|---|---|---|
| 2008/0249444 A1 | 10/2008 | Avitable et al. |
| 2010/0117039 A1 | 5/2010 | Perrett et al. |
| 2014/0109560 A1 | 4/2014 | Ilievski et al. |
| 2014/0224018 A1 | 8/2014 | Whitesides et al. |
| 2015/0351936 A1* | 12/2015 | Mosadegh ............... B25J 15/12 623/26 |

* cited by examiner

ACTUATORS

RELATED APPLICATION

This application is a national Stage Entry of PCT International Application No. PCT/US16/61078 filed Nov. 9, 2016, which claims priority to U.S. Provisional Application No. 62/254,461, filed Nov. 12, 2015, the contents of which are incorporated herein by reference in their entirety.

GOVERNMENT FUNDING CLAUSE

This invention was made with support from the United States government under Grant Nos. DE-SC0000989 and DE-FG02-00ER45852 awarded by the Department of Energy. The United States government has certain rights to this invention.

INCORPORATION BY REFERENCE

All patents, patent applications, and publications cited herein are hereby incorporated by reference in their entirety in order to more fully describe the state of the art as known to those skilled therein as of the date of the invention described herein.

BACKGROUND

Actuators have come a long way since the invention of rotary motors, which set the foundation for robotics and marked the dawn of the age of automation and industrialization. The drastic improvement in performance of hard actuators nowadays is only matched by the large number of emerging soft actuators, which demonstrate functionalities tantamount to or more expansive than that of their hard counterparts.

"Muscle" is the almost universal actuator in animals. In efforts to mimic aspects of the mechanics of (if not the mechanism of action of) biological muscle, a large range of synthetic structures has been explored, but none has successfully replicated the essential features of muscle. Muscle has three features that have remained difficult to replicate: muscle i) maintains roughly a constant volume upon contraction; ii) shows a useful compromise between speed of actuation and force applied during actuation; iii) has mechanical properties (e.g., stiffness and density) that are compatible with the requirements of animals.

McKibben actuators, developed in the 1950s, were examples of muscle-mimetic structures. These actuators comprise a rubber balloon, constrained in volume by an inelastic mesh. On pressurization, the balloon inflates anisotropically (with a motion that reflects the structure and mechanics of the surrounding mesh), and this expansion results in useful motion. The properties of the fiber reinforcement (i.e., the density of the weave, and the strength of the fibers) dictate the strain (typically 25%) and load (typically 800~1300 kPa) the actuator can produce for a given pressure. McKibben actuators have many practical applications, but suffer from three disadvantages: i) their inherent dry friction, and the non-elastic deformation of the mesh balloon, causes hysteresis; this hysteresis renders precise positional control difficult; ii) they often cannot be actuated if the applied pressure is below a certain "threshold pressure"; this threshold may prevent the generation of low force; and iii) the application of a pressure that is too high (typically ~500 kPa) can make the balloon bulge through the mesh, and perhaps burst.

Soft actuators are important for their ability to contact delicate, soft, and irregularly-shaped objects (i.e., humans and animals, fruit, produce), because they distribute forces across the surface of the objects, and because they are fabricated of compliant rather than unyielding materials and structures. They also offer an attractive approach to simplifying controls, since they make it possible—in some circumstances—to substitute the properties (and especially non-linearities such as "snap-through") of materials and structures for some of the control loops, sensors, and actuators of hard robots.

Pneumatically-actuated soft machines are being actively developed, but as a clan, they have two characteristics that can limit their use in some applications: i) they can burst when over-pressurized, and therefore may be dangerous or unreliable when used outside their specified operational ranges; and ii) most increase in volume when pressurized, and thus cannot be used in applications in confined spaces. Thus, there remains a need for new and more effective actuators.

Soft, linear actuators (those that generate motions in a straight line—for example, the muscles of animals) have emerged from evolution as the best solution for moving limbed organisms such as vertebrates and arthropods (as well as many organisms without limbs, such as mollusks, annelids, and jellyfish) in an unstructured environment. Their compliance enables adaptive interactions with the environment, and non-damaging (if required) contact with one another. At the same time, this compliance reduces the cost to the organism of precise controls and feedback loops. Linear actuation is also particularly compatible with a limbed body-plan in its geometric adaptability since this body-plan is often based on rigid or semi-rigid structural elements (the skeleton), which move relative to one another by linear contraction of muscles around fulcra (e.g., joints). Hard, human-engineered machines now often use the rotary motion of electric motors, although pneumatic and hydraulic pistons (based on force generated by expansion of hot gas, pressurized air, vacuum, or pressurized liquid), other actuators (e.g., magnetic solenoids), and transducers of biomechanical forces (e.g., screwdrivers) are also important. A key characteristic of soft machines is that they can be made collaborative (e.g., intrinsically safe in close proximity to humans).

Devices or systems that generate a mechanical advantage—levers, gears, chain drives, block and tackles, and others—are useful in amplifying either force or displacement in hard machines. Humans and other vertebrates also use hard levers—system of bones, articulated joints, and tendons—to amplify the displacement that muscles generate (albeit at the cost of reduced force). A device that generates a mechanical advantage in a soft system would expand the capabilities of soft robots and machines. The compliance of pneumatic soft actuators allows them to distribute their stress over large areas, but it also means the pressure output of these systems is often limited by their pressure input, and thus also by the mechanical characteristics—especially the Young's Modulus—of the material of which they are made. A soft pneumatic actuator designed to generate a mechanical advantage would help to overcome this limitation. Making artificial, soft, linear actuators that mimic the structure and rival the performance of natural muscles has, however, proven a challenging task.

The use of vacuum, and the reversible buckling of soft elastomeric beams, as the basis for actuators is described in PCT/US15/40896, filed Jul. 17, 2015, the contents of which are incorporated herein by reference. These actuators include pneumatic chambers with arrangements of soft elastomeric beams inside. When a vacuum is applied to the pneumatic chamber, the arrangement of beams allows the structure to collapse asymmetrically along one axis; the difference in pressure between the atmosphere and the partial vacuum inside the chamber is converted to an output stress in the direction of motion. A limitation of these actuators is that the differential pressure applied to its chambers limits the stress it can produce.

SUMMARY

Described herein are shear force actuators, e.g., pennate-muscle inspired vacuum actuators ("PIVA"; also referred to as shear-VAM (shear-mode vacuum-actuated machine)), whose output stress generated by the actuator is not limited by the atmospheric pressure or the input differential pressure.

As used herein, pennate-muscle inspired vacuum actuator ("PIVA") and shear-mode vacuum-actuated machine ("shear-VAM") are used interchangeably.

In some embodiments, the actuators described herein are inspired by pennate muscle and can produce an actuation stress much higher than the input differential pressure at a cost of actuation strain. Without wishing to be bound by any particular theory, it is believed that the actuators described in one or more embodiments transfer the horizontal compressive force to a vertical shear force via soft beams/lever. Thus, in certain embodiments, a force applied to the horizontal surfaces of an actuator, e.g., a PIVA, is converted to a vertical one, thus enabling an almost arbitrarily high actuation stress to be generated.

In one aspect, a shear force actuator is described, including:
- two substantially parallel first structural components disposed along a first axis;
- a plurality of substantially parallel second structural components disposed between and bridging the two first structural components;
- a plurality of joint sections, each joining the second structural component with the first structural components at an oblique angle of between 0 and 90 degrees, to define a plurality of cells, each capable of being connected with a fluid inflation or deflation source;
- a surface covering the remaining surfaces of the cells in a fluid-tight manner; wherein
- at least one of the joint sections, the first structural components, and the second structural components is elastic so that cell collapses upon removal of fluid from the cell to generate a linear force along the first axis.

In any one of the embodiments described herein, the joint section is elastic.

In any one of the embodiments described herein, the second structural component is elastic.

In any one of the embodiments described herein, the two first structural components are not elastic.

In any one of the embodiments described herein, the two first structural components are made of a flexible but inextensible material.

In any one of the embodiments described herein, the first structural components and/or the second structural components are made of non-deformable hard materials, and the joint section is made of deformable soft material or a rotatable a hard hinge.

In any one of the embodiments described herein, the hard hinge is made of a hard material selected from the group consisting of metal, plastic, glass, wood, and stone.

In any one of the embodiments described herein, the joint section is section where the first and second components are coupled with a hinge, a pivot, or other rotational coupling mechanism. In any one of the embodiments described herein, the joint section is a hinge, a pivot, or other rotational coupling mechanism coupling the first and second components.

In any one of the embodiments described herein, the oblique angle is about 30, 40, 45, 60, 65, 70, or 75 degree.

In any one of the embodiments described herein, the shear force actuator includes more than 2, 5, 20, 50, or 100 second structural components.

In any one of the embodiments described herein, the plurality of cells are configured to be connected to each other and configured for connection with the same fluid inflation or deflation source, but are otherwise isolated from the atmosphere.

In any one of the embodiments described herein, the first axis is horizontal or vertical.

In any one of the embodiments described herein, the surface is elastomeric or hard.

In any one of the embodiments described herein, the surface is hard and at least one of the first and second structural components is able to slide, i.e., slidable, along the surface without breaking the fluidic seal.

In any one of the embodiments described herein, the surface is planar.

In any one of the embodiments described herein, the contact between the surface and the first and second structural components is lubricated with a lubricant.

In any one of the embodiments described herein, the cell is configured to collapse upon the removal of the fluid and return to its original position when the deflated cell is re-inflated.

In any one of the embodiments described herein, the first and/or second structural components have high-aspect ratio.

In any one of the embodiments described herein, the joint section and/or the second structural component are made from an elastic polymer.

In any one of the embodiments described herein, the fluid is a gas or liquid.

In any one of the embodiments described herein, the fluid is air.

In any one of the embodiments described herein, the cell is connected to a gas inflation/deflation source via a fluid chamber.

In any one of the embodiments described herein, the cell is in the form of a rod, slit, sphere, cube, hexahedron, or cylinder.

In any one of the embodiments described herein, the second structural component or its cross-section is in the form of a pillar, a lever, or beam.

In any one of the embodiments described herein, the first structural component or its cross-section is in the form of a pillar, a lever, or beam.

In any one of the embodiments described herein, the fluid inflation or deflation source is a gas pump, a gas vacuum, or a gas pump and vacuum.

In any one of the embodiments described herein, the shear force actuator further includes a hard and/or soft body portion.

In another aspect, an actuator is described, including a plurality of shear force actuators each according to any of the embodiments disclosed herein.

In yet another aspect, a method of actuation is described, including:

providing the shear force actuator of any one of the embodiments disclosed herein; and deflating the cells to cause the cells to collapse to generate a linear force.

It is contemplated that any embodiment disclosed herein may be properly combined with any other embodiment disclosed herein. The combination of any two or more embodiments disclosed herein is expressly contemplated.

In certain embodiments, the actuator disclosed herein is a shear force actuator, i.e., a linear actuator that generates a linear force by converting a partial vacuum applied to it into a shear force. In certain specific embodiments, the shear force actuator is a soft actuator. As used herein, "soft actuator" refers to an actuator with at least one portion of its body being soft. As used herein, "soft body" refers to the body of the soft actuator or a portion of the soft actuator that is soft, and may be involved in the actuation movement of the soft actuator. As used herein, "soft" refers to the act that the body of the actuator or a portion thereof may yield to pressure or weight and/or change shape in response to a force applied to the body. However, the soft actuator or soft body, as used herein, may have one or more portions of its body being hard or may be connected with a hard part or device.

As used herein, pennate-muscle inspired vacuum actuator (PIVA) or shear-mode vacuum-actuated machine (shear-VAM) is one specific example of the actuator (e.g., shear force actuator) described herein. In certain embodiments, PIVA is a soft actuator. In certain embodiments, a shear force actuator in general can be either soft or hard. As used herein, pennate-muscle inspired vacuum actuator (PIVA) and shear-mode vacuum-actuated machine (shear-VAM) are used interchangeably.

Unless otherwise defined, used or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein.

It will be understood that the spatially relative terms, as well as the illustrated configurations, are intended to encompass different orientations of the apparatus in use or operation in addition to the orientations described herein and depicted in the figures. Spatially relative terms, such as "above," "below," "left," "right," "in front," "behind," and the like, may be used herein for ease of description to describe the relationship of one element to another element, as illustrated in the figures for illustration purposes only, which should not be construed as limiting. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly. Further still, in this disclosure, when an element is referred to as being "linked to," "on," "connected to," "coupled to," "in contact with," etc., another element it may be directly linked to, on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise. Additionally, the terms, "includes," "including," "comprises" and "comprising," specify the presence of the stated elements or steps, but do not preclude the presence or addition of one or more other elements or steps.

DESCRIPTION OF THE DRAWINGS

The invention is described with reference to the following figures, which are presented for the purpose of illustration only and are not intended to be limiting. In the Drawings:

FIG. 6a) shows the relationship between the distance of actuation $\Delta h$ (in mm) and the force of actuation F (in N) on shear-VAMs, measured on seven different samples made of Elastosil (E=520 kPa). A sufficient difference of pressure $\Delta P=90$ kPa$>\Delta P_{crit}$ is applied to collapse the void chambers completely. FIG. 6B shows the relationship between the maximum force of actuation $F_{max}$ of shear-VAMs (in N) and the Young's Modulus E (in kPa) of the elastomer used in fabricating the shear-VAMs.

FIG. 7A shows the shear-VAM lifts the weight for a distance of $\Delta$h upon actuation while F<$F_{max}$. FIG. 7b) shows the shear-VAM lowers the weight for a distance of $\Delta$h' upon actuation while F>$F_{max}$. The difference of pressure applied is $\Delta P=90$ kPa.

FIG. 9A shows a schematic diagram marking different dimensions of a shear-VAM (length L, beam length a, width b, beam angle α, and lateral area A). FIGS. 9B-9C show schematic drawings illustrating an increase in either the length L (FIG. 9B) or width b (FIG. 9C of a shear-VAM increases its lateral area A, and thus increasing the force of actuation F (Equation 4). FIG. 9D shows the relationship between the force of actuation F of shear-VAMs of two different lengths L=62 mm and 32 mm (each connected to a fixed strain gauge), and the difference of pressure $\Delta P$ (in kPa) applied across these shear-VAMs (see descriptions below and FIG. 8 for details of this measurement). Data shown are mean±S.D. (n=7 repeated measurements). FIG. 9E shows the maximum force of actuation of shear-VAMs $F_{max}$ (in N) made of Ecoflex (E=43 kPa) vs. their length L.

FIG. 11A shows two shear-VAMs in an agonist-antagonist arrangement can drive a paddle back and forth. The paddle can pivot around its connection backwards, but not forward. This mechanism can be used in a soft machine that paddles. FIG. 11B shows a soft robotic swimmer with a paddle powered by two shear-VAMs in an agonist-antagonist arrangement. Scale bars are 1 cm-long. A quarter coin in the water also marks the scale.

FIG. 12A a schematic describing the setup used for testing. FIG. 12B P-V curves of a shear-VAM fabricated in Elastosil lifting a 500 g weight. The actuation curve is marked in black, and the return curve is marked in red. The shaded area $E_{in}$ represents the fluidic energy input via the syringe pump.

DETAILED DESCRIPTION

Figure 1A:
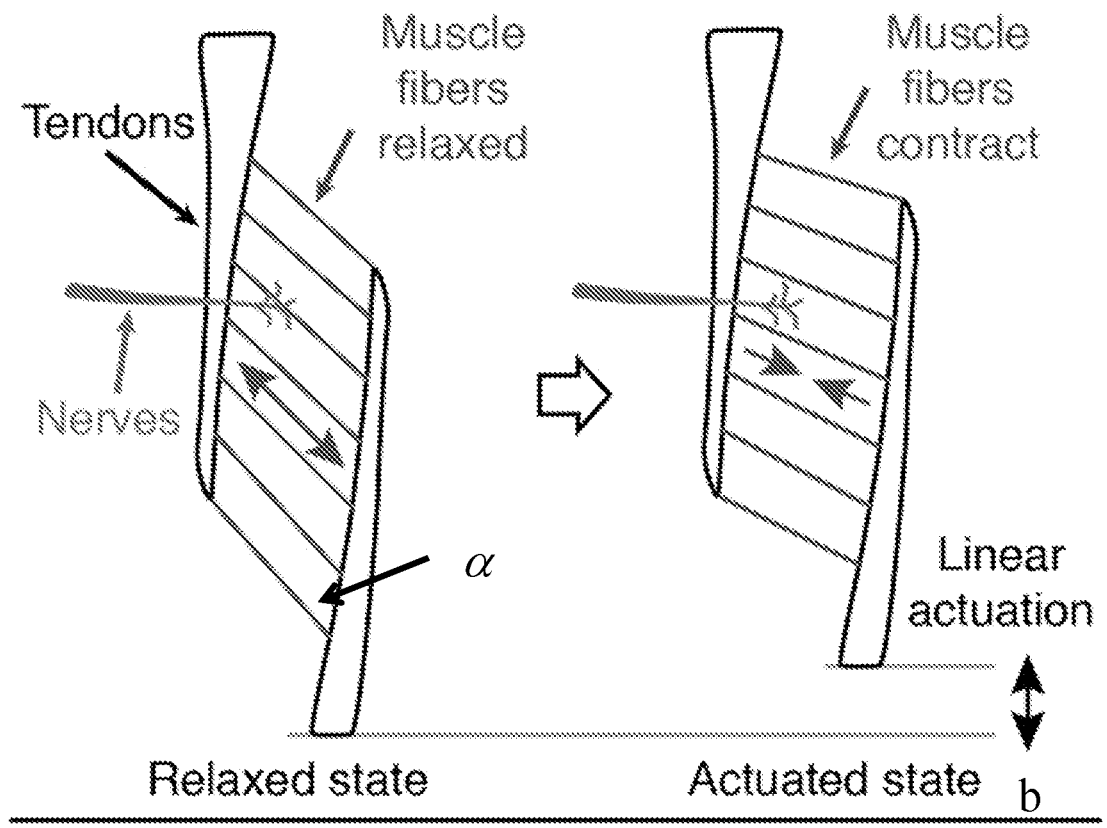
FIG. 1A shows the schematics of the mechanism of motion of pennate muscle converting horizontal tensile force to a vertical shear force, according to one or more embodiments described herein.

Muscles in humans and animals are hierarchical structures, organized on scales from nanometers (individual strands of myosin and molecules of actin) to meters (structures of macroscopic muscle in large animals). They adopt different shapes and arrangements of fibers in order to adapt to the requirements of different types of mechanical performances (high actuation stress, high actuation strain, high speed, etc.) across the body. One particularly useful strategy is to adopt a "pennate structure"—that is, to arrange the muscle fibers at an angle α to the line of action (i.e., direction b), instead of parallel to it, and stack them along the direction of actuation (FIG. 1A). This geometry allows the muscle to: i) convert a force applied at an angle to the tendons on the side of the muscle to a force parallel to the tendons (i.e., direction b), ii) pack more muscle fibers into a given apparent cross-sectional area than muscle with parallel fiber arrangement, and iii) generate a larger actuation stress (defined as the force generated by the muscle divided by the apparent cross-sectional area) compared to a parallel muscle fiber arrangement. This increased stress comes, however, at the cost of a smaller actuation strain (defined as the change of muscle length in the direction of actuation divided by total muscle length).

The compliance of pneumatic soft actuators allows them to distribute their stress over large areas, but it also means the pressure output of these systems is often limited by their pressure input, and thus also by the mechanical characteristics—especially the Young's Modulus—of the material of which they are made. A soft pneumatic actuator designed to generate a mechanical advantage would help to overcome this limitation.

Figure 1B:
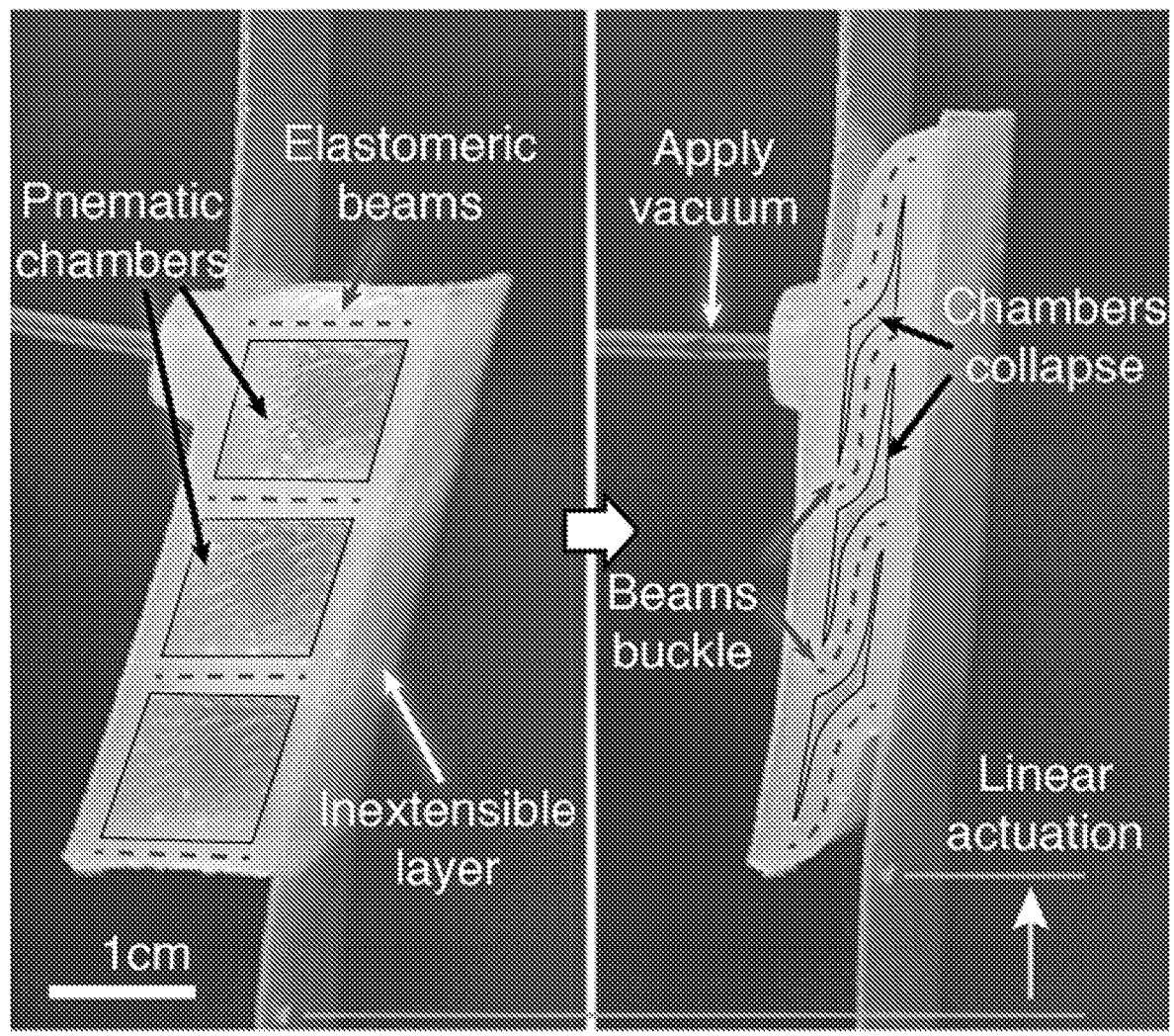
FIG. 1B shows the schematics of a pennate-muscle inspired vacuum actuator (PIVA) (also referred to as a shear-mode vacuum-actuated machine (shear-VAM) demonstrating the mechanism of motion of a PIVA, according to one or more embodiments described herein.
Figure 1C:
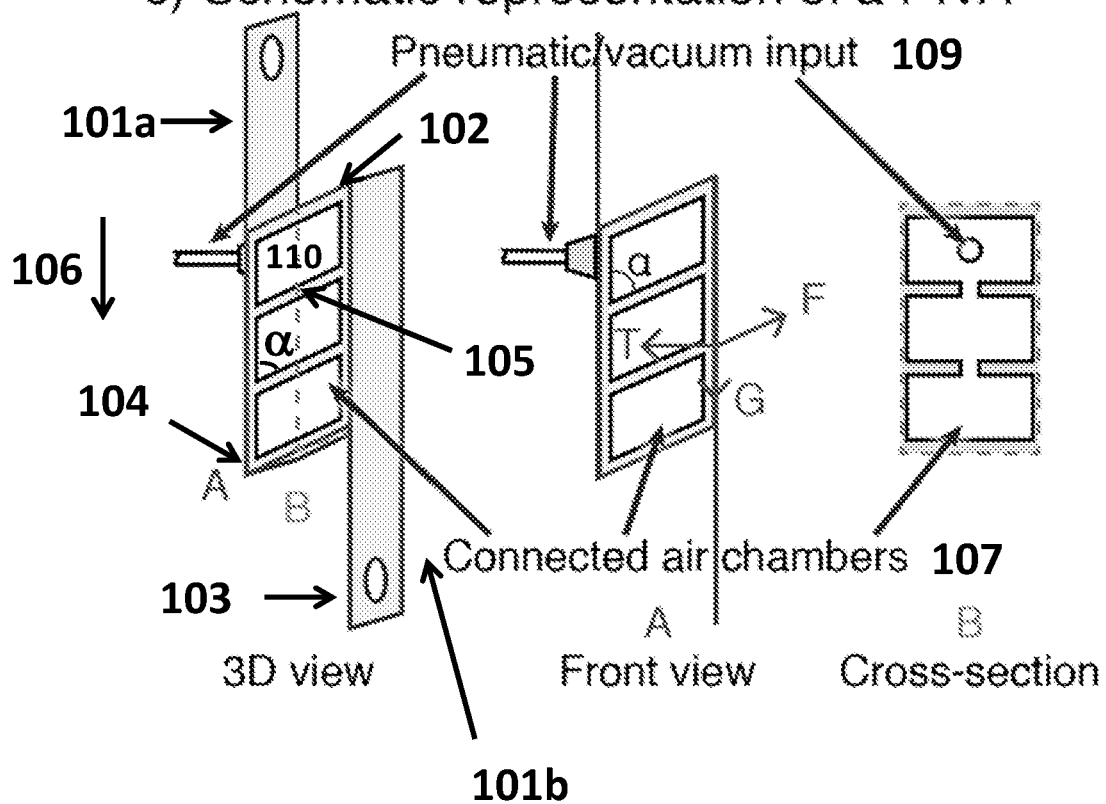
FIG. 1C shows a schematic representation of a pennate-muscle inspired vacuum actuator (PIVA), according to one or more embodiments described herein.
Figure 1D:
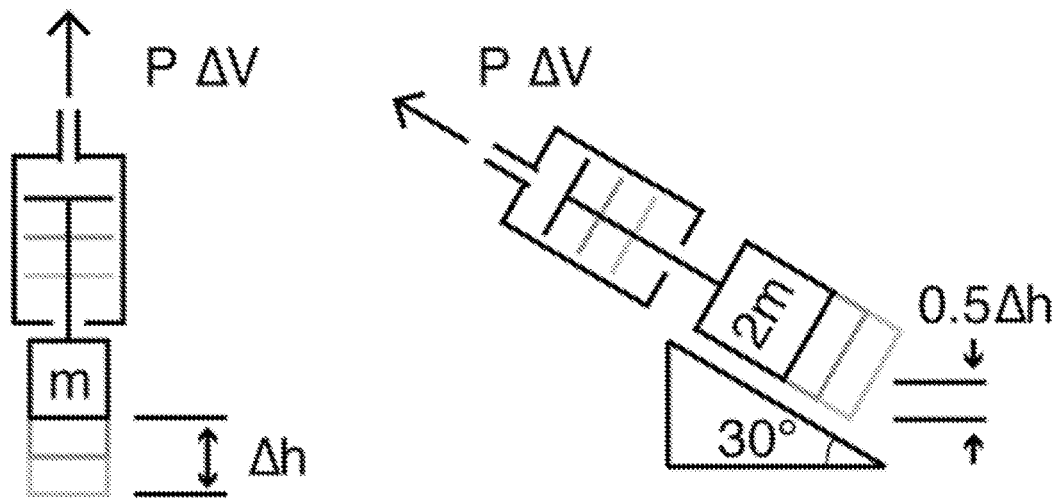
FIG. 1D shows an example of mechanical advantage in pneumatic actuation, according to one or more embodiments described herein.

In some embodiments, mechanical advantage is introduced into a soft pneumatic actuator. FIG. 1D is a conceptual picture summarizing this concept. Compared to lifting a weight (generating mg $\Delta$h work) directly using a pneumatic piston (supplying p $\Delta$V work), pulling a weight on a slope increases the weight m pulled per applied pressure P, while decreasing the height $\Delta$h per volume change $\Delta$V. The objective here is to realize this mechanical advantage in a soft actuator without using an external slope.

In one aspect, a shear force actuator is described, including: two substantially parallel first structural components disposed along a first axis; a plurality of substantially parallel second structural components disposed between and bridging the two first structural components; a plurality of joint sections, each joining the second structural component with the first structural components at an oblique angle of between 0 and 90 degree to define a plurality of cells, each capable of being connected with a fluid inflation or deflation source; and an elastic surface covering the remaining surfaces of the cells in a fluid-tight manner; wherein at least one of the joint section, the first structural components, and the second structural components, and elastic so that cell collapses upon removal of fluid from the cell to generate a linear force along the first axis.

In some embodiments, the shear force actuator is a vacuum-actuated shear force actuator. In some embodiments, the shear force actuator is a positive-pressure shear force actuator.

In some embodiments, the shear force actuator is a soft actuator having a soft body. In other embodiments, the shear force actuator has a hard body. In still other embodiments, the shear force actuator's body is partially hard and partially soft. As used herein, the phrase "substantially parallel" refers to the scenario in which two first or second structural components are at 180 degrees, or 165, 170, 175, 176, 178, or 179 degrees or from 165-180 degrees, from 170-180 degrees, or 175-180 degrees. In some embodiments, the phrase "substantially parallel" refers to the scenario that the two first or second structural components deviate from being parallel by less than 35°, 30°, 25°, 20°, 15°, 10°, 5°, 4°, 3°, or 1°, or in a range bounded by any two values disclosed herein.

In some specific embodiments, a new design of a soft linear actuator that generates a tunable mechanical advantage is described, which may be referred to as pennate-muscle inspired vacuum actuator (PIVA) or shear-mode vacuum-actuated machine (shear-VAM). In some specific embodiments, described herein is a shear force actuator that is similar in form and function (but not in molecular mechanism) to pennate muscles (FIG. 1B)—it demonstrates a similar strategy to pennate muscles of increasing stress output via stacking actuators vertically. As shown in FIG. 1B, a PIVA comprises two flexible but inextensible strips bridged by a series of obliquely-positioned parallel elastomeric beams (tilted parallel beams). The spaces in between the beams are sealed pneumatically with a thin elastomeric membrane, forming void chambers within. In some embodiments, these chambers are connected to a single external vacuum source or fluid source (or, in more complex devices, multiple independently controllable sources). In some embodiments, through a network of channels embedded in the structure, a shear-VAM or PIVA operates by reducing the pressure of void chambers in an elastomeric structure to below that of atmospheric pressure (that is, to negative pressure, or partial vacuum). When the chambers are evacuated, ambient atmospheric pressure compresses the two inextensible strips, which move together in the direction of actuation. The design—in which the beams bend more easily than they compress—causes these beams to tilt further; this increase in tilt, in turn, causes the strips to translate parallel to one another, and to generate force (see FIG. 1B).

This design has a feature similar to that of pennate muscle: the stress it can generate increases as the device increases in length, e.g., the length of the inextensible strips increases, rather than in cross-sectional area (that is, the dimension of the parallel elastomeric beams). These structures belong to a new class of soft pneumatic actuators or machines—which are more collaborative, often more adaptive to irregular targets, and sometimes simpler to control—than more familiar hard machines.

In some embodiments, the soft pneumatic actuators powered by negative pressure (vacuum) rather than positive pressure can be referred to as vacuum-actuated machines (VAMs). These devices allow a range of functions that can sometimes be difficult to achieve by their conventional pressure-driven counterparts. Examples of VAMs includes rotary actuators that combine vacuum and reversible buckling of elastomeric beams as their mechanism of action (rotary-VAMs) and linear actuators (using the same mechanism) that mimic the performance—and many useful functions—of human muscle (linear-VAMs).

Vacuum-actuated machines (VAMs) such as shear-VAMs are safer around humans than many "hard" actuators, and even ostensibly soft actuators that operate under high positive pressure (e.g., McKibben actuators and many of their relatives). Actuators powered by pneumatics are also safer and less likely to fail than those powered by high voltages (e.g., actuators made with dielectric elastomers can fail by dielectric breakdown). They are also surprisingly efficient thermodynamically, and are durable over millions of cycles. Upon application of vacuum to its pneumatic chambers, the internal structures of shear-VAMs convert a horizontal compressive stress to a vertical shear stress. By physical analogy to pennate muscle, shear-VAMs can be stacked vertically to generate higher stress.

A feature of the previously-described actuator in PCT/US15/40896 is that a maximum difference in pressure between the atmosphere and the partial vacuum applied to the chambers (the maximum being the atmospheric pressure) limits the stress it can produce. In contrast, the pennate-muscle inspired vacuum actuator converts the force applied to its side-surfaces into a force parallel to its side-surfaces, thus allowing a very high stress to be generated. In certain embodiments, sufficient surface area on the sides of the actuator can be achieved by increasing its length. Without wishing to be bound by any theory, it is believed that surface area on the side of PIVA equals the width of the strip times the height of the body of the actuator. As such, increasing the length/height of the actuator will result in a higher side-surface area, if the cross sectional geometry of the PIVA is kept constant. This is under the presumption that the requirement that increased stress comes at the cost of reduced strain is acceptable, since the amount of lift-height a PIVA generates is determined by the length and initial angle of the oblique beams, increasing the length of the actuator will not affect this lift-height. Since the effective strain of the PIVA equals lift-height/total length, increasing the total length of the actuator will proportionally decrease the strain of the actuator.

In some embodiments, the soft actuator as described herein, e.g., a shear-VAM, is described with reference to FIG. 1C. As shown in FIG. 1c, the shear-VAM includes two substantially parallel first structural components $101a$ and $101b$ (e.g., two flexible but inextensible strips (1.5 mm thick, 17 mm wide, and 10 mm apart)) disposed along a first axis 106. A plurality of substantially parallel second structural components 105 (e.g., four tilted parallel elastomeric beams (1.8 mm wide, 8.9 mm long, at 63° angle to the strips, and spaced in 10 mm-intervals along the strips) are disposed between and bridging the two first structural components $101a$ and $101b$. A plurality of joint sections 104 each joins the second structural component 105 onto the first structural components $101a$ and $101b$ at an oblique angle $\alpha$ of between 0 and 90 degree to define a plurality of cells 107. Each of cells 107 is connected with a fluid inflation or deflation source through a pneumatic/vacuum input 109. The remaining surfaces, e.g., surface 110, are covered in a fluid-tight manner (e.g., by an elastic membrane). In some embodiments, the joint section and/or the second structural components are elastic, so that cell collapses upon removal of fluid from the cell to generate a linear force along the first axis 106. In some embodiments, the first structural components are made of a flexible but inextensible material or composite such that it can transduce and sustain the linear force through it without substantial extension or deformation. In some embodiments, the first structural components and/or the second structural components are made of hard materials and cannot deform, but the joint section is made either of soft material that can deform, or of a hard hinge that can rotate, and the joint thus allows the structure to transform. FIG. 1C shows that 3D view (left), front view (middle), and the cross-section view (right) of the shear-VAM (also can be referred to as PIVA).

In some embodiments, a nylon mesh embedded in an elastomer—Ecoflex 00-30 (Young's modulus E=43 kPa), Dragon Skin 10 Slow (E=153 kPa), or Elastosil M4601 (E=520 kPa)—is used for the inextensible layer. The same elastomer in the elastomeric beams can be used in shear-VAMs. The empty spaces in between the beams were converted into enclosed chambers by sealing (front and back) with thin membranes made of the same elastomer (1 mm thick). The final structure comprises a pneumatic structure with several chambers connected to a common source of negative pressure (e.g., vacuum, or pressure less than the ambient pressure). The beams each had an opening in the middle (a 3 mm-wide slit) such that the chambers were pneumatically connected. The chambers were further connected to an external source of vacuum through a piece of tubing that pierces one of the strips. (See FIG. 5 for details of fabrication.)

In some embodiments, the joint section and/or the second structural component are elastic. The phrase "joint section," as used herein, refers to the portion of the device where the first and second structural components are joined together to create the oblique angle of the device. In some embodiments, the joint section is a section where the first and second components are glued or otherwise bonded together. In some embodiments, the joint section is section where the first and second components are coupled with a hinge, a pivot, or other rotational coupling mechanism. In some embodiments, the joint section is used to refer to a hinge, a pivot, or other rotational coupling mechanism which couples the first and second components. This will allow the cell to be collapsible under removal of the fluid from the cell. As a result, the two substantially parallel first structural components will move towards each other to generate a linear force along the first axis (see, FIG. 1B and FIG. 1C), thus transferring the horizontal movement to a vertical movement. In some embodiments, the two first structural components are not elastic and maintain their parallel orientation after the collapse of the cells.

In some embodiments, the shear force actuator's soft body contains a plurality of cells inside the soft body. As used herein, the term "cell" refers to an enclosed space within the body of the shear force actuator. The cells are configured for connection with an external fluid inflation and/or deflation source. The geometry of the cell can take on any form or shape. In some embodiments, the cell is in the form of a rod, slit, triangular prisms, square prisms, spheres, rectangular prisms cylinder, or a cylinder of oval cross-section shape. In certain embodiments, other than the connection to the fluid inflation and/or deflation source, the cell is isolated from the outside atmosphere. In some embodiments, the cells are all connected to the same fluid source. In other embodiments, at least two of the cells are connected to different fluid sources so that the two or more cells may be vacuumed/inflated independently by controlling the different fluid sources. In certain embodiments, two or more cells are connected to each other. The soft body or portions thereof define the boundaries, e.g., walls, of the cells. In certain embodiments, the first and second structural components make up at least four of the boundaries or surfaces, e.g., walls, of the cell. In certain embodiments, elastic surface(s) cover/form the remaining two surfaces/walls of the cell. In some embodiments, the cell is configured to collapse upon the removal of the fluid and return to its original position when the deflated cell is re-inflated.

In some embodiments, the first and/or second structural components have high-aspect ratio. As used herein, aspect ratio refers to the ratios of the long dimension to the short dimension of an object or particles. An aspect ratio of more than one is generally referred to as high aspect ratios. In certain embodiments, the second structural component has an aspect ratio of more than 1:1, 2:1, 3:1, 4:1, 5:1, 10:1, or 20:1, or in the range denoted by any two values described herein. Other suitable high aspect ratios are contemplated.

In certain embodiments, the first and/or second structural components are in the form of pillars, levers, or beams. As used herein, the term "pillar", "lever," and "beam" all refer to a structure that has two ends, which, under a compressive force applied across the two ends, which are built to be strong enough to resist the compressive force across it and maintain its shape during the actuation process.

Any known elastic material can be used to make the joint section and the second structural component. In some embodiments, the joint section is a joint element joining the first and second structural components. In some embodiments, the elastic material is an elastic polymer. Any elastic polymer known in the art can be used. Non-limiting examples of the elastic polymer include natural rubber, silicone rubbers, polyurethane rubbers, isoprene rubber, butadiene rubber, butyl rubber, styrene-butadiene rubber, nitrile rubber, ethylene propylene rubber, epichlorohydrin rubber, polyacrylic rubber, fluorosilicone rubber, fluoroelastomers, perfluoroelastomers, polyether block amides, chlorosulfonated polyethylene, ethylene-vinyl acetate, thermoplastic elastomers, proteins resilin and elastin, polysulfide rubber, elastolefin, etc. In some embodiments, the elastic material is Ecoflex, Stratasys PolyJet 3D printed soft material, Elastosil, PDMS, or another material that is elastic and airtight. In other embodiments, the first and second structural components are made of hard materials, and the joint is a hinge that is made of a hard material. The hard material can be any structural material with limited to no deformation capabilities, such as various metal, plastic, glass, wood, stone, etc.

In certain embodiments, the oblique angle is about 30, 40, 45, 60, 65, 70, or 75 degree, or in a range bounded by any two values disclosed here. In certain specific embodiments, the oblique angle is about 55, 60, 65 degree, in a range bounded by any two values disclosed here. In certain specific embodiments, the oblique angle is about 60. In certain embodiments, the first axis is horizontal or vertical.

In certain embodiments, the remaining surface of the cell is covered and sealed by a surface, to result in a fluid-tight cell. The surface can be elastic, e.g., a rubber membrane. The use of other elastic surface material known in the art is contemplated. In some embodiments, the remaining surface of the cell is covered and sealed by a surface made of hard materials. At least one of the first and second structural components are not fixated to the surface and can slide along it, without breaking the fluidic seal. In some embodiments, the surface is planar. In some embodiment, the contact between the hard surface and the first and second structural components are lubricated with a lubricant.

Applicants have found that the output of the linear actuation force can be proportional to side surface area of the actuator.

Figure 2A:
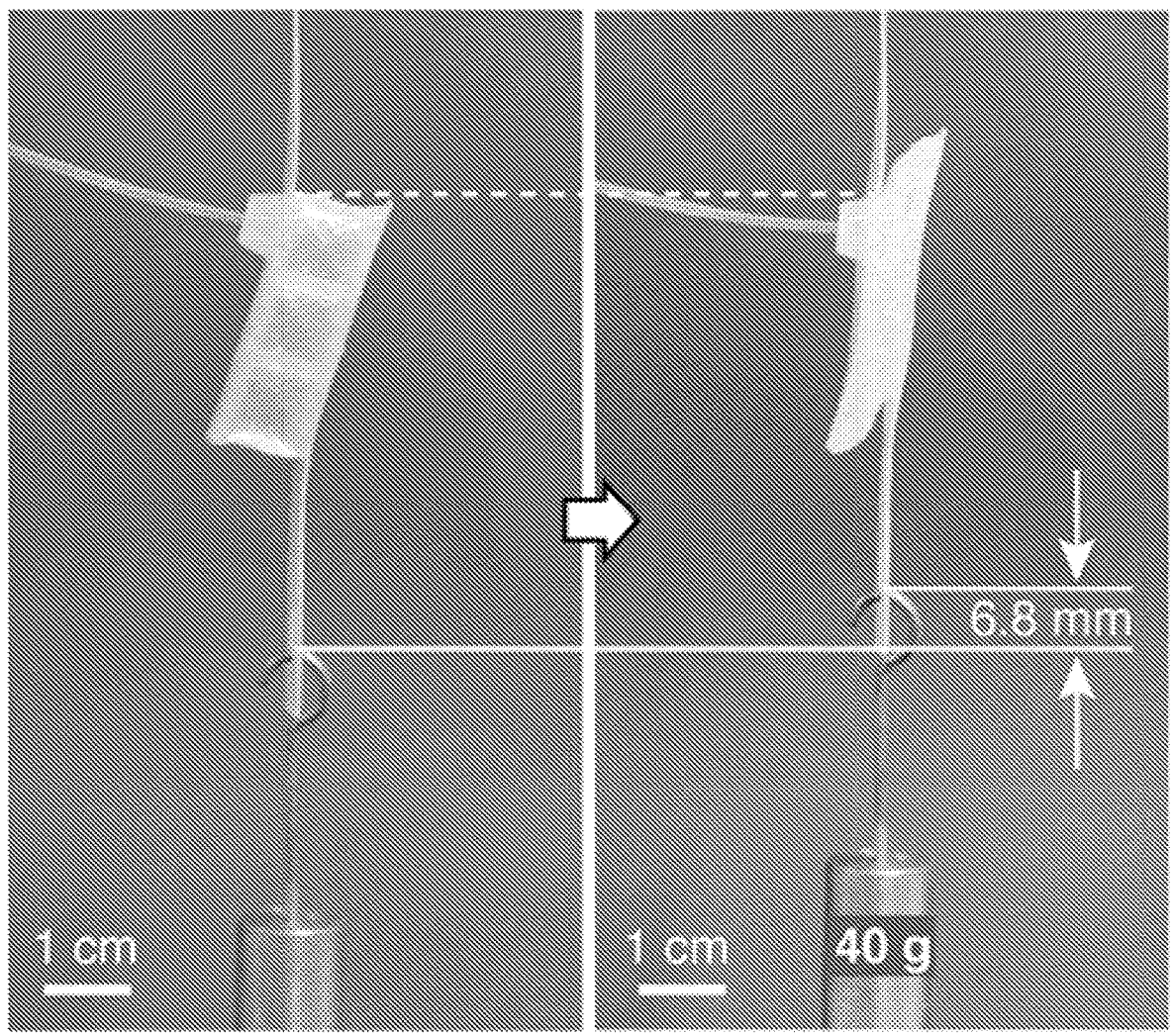
FIG. 2A illustrates a shear-VAM (also referred to as pennate-muscle inspired vacuum actuator (PIVA)) made of Ecoflex (E=43 kPa) with four beams lifting a 40-g weight, according to one or more embodiments described herein.
Figure 2B:
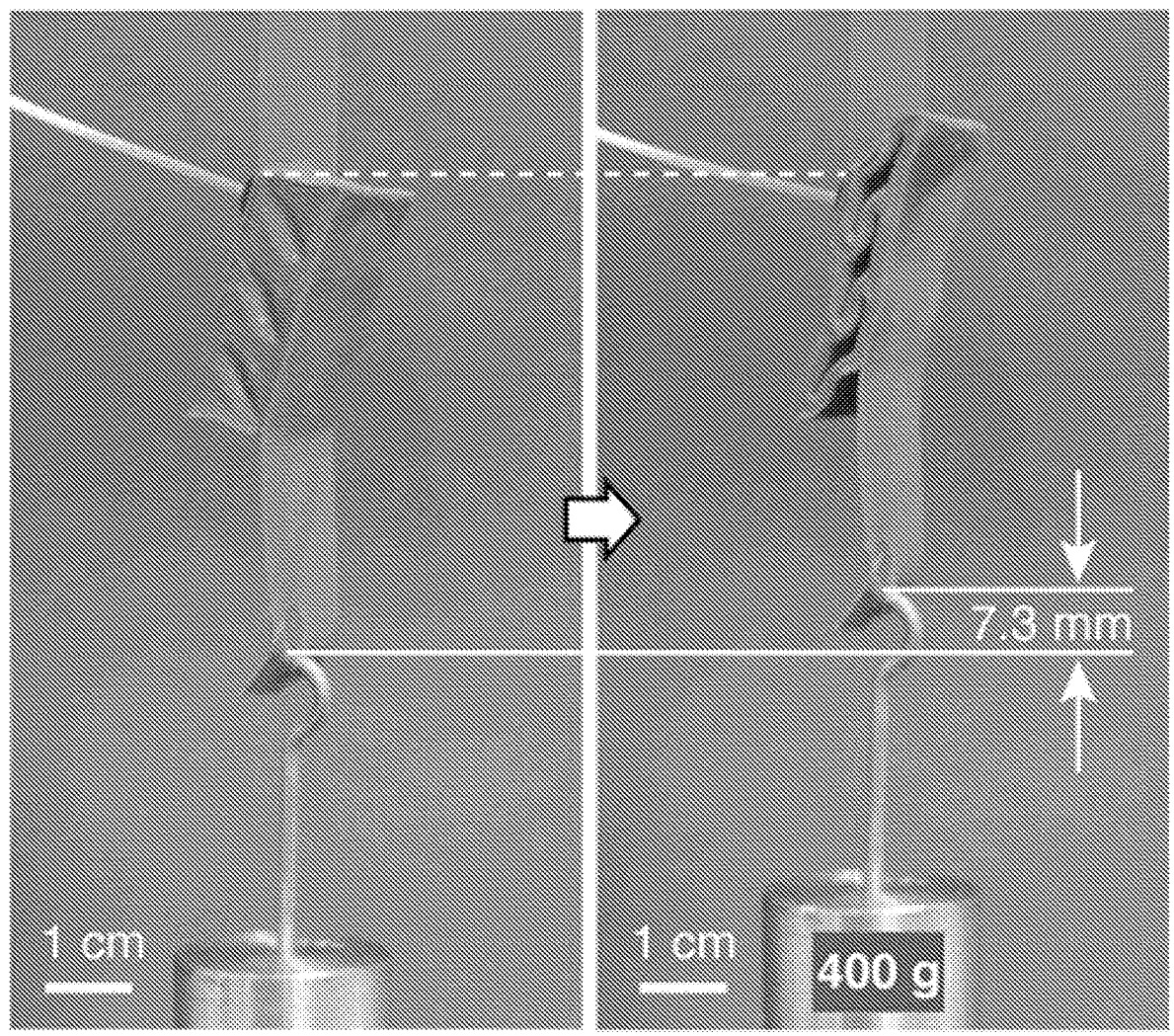
FIG. 2B illustrates a shear-VAM (also referred to as a pennate-muscle inspired vacuum actuator (PIVA)) of the same geometry as FIG. 2a), but made of Elastosil (E=520 kPa) lifting a 400-g weight, according to one or more embodiments described herein.

In certain embodiments, the output of the soft linear actuation force may be increased by using a stiffer material to make the joint section and/or second structure component. In certain embodiments, the output of the soft linear actuation force is proportional to the modulus of material resulted (e.g., the stiffness of the material). Non-limiting examples of the suitable materials include Ecoflex and Elastosil. As shown in FIGS. 2A-B, a shear-VAM (PIVA) fabricated from a stiffer elastomer can lift a heavier weight. As shown in FIG. 2A, a shear-VAM made of Ecoflex (E=43 kPa) with four beams can lift a 40-g weight. As shown in FIG. 2B A shear-VAM the same geometry but made of Elastosil (E=520 kPa) can lift a 400-g weight. Shear-VAMs exert greater force when fabricated in stiffer elastomers—an approximately ten-fold increase in the modulus of material resulted in an approximately ten-fold increase in maximum load.

Figure 3A:
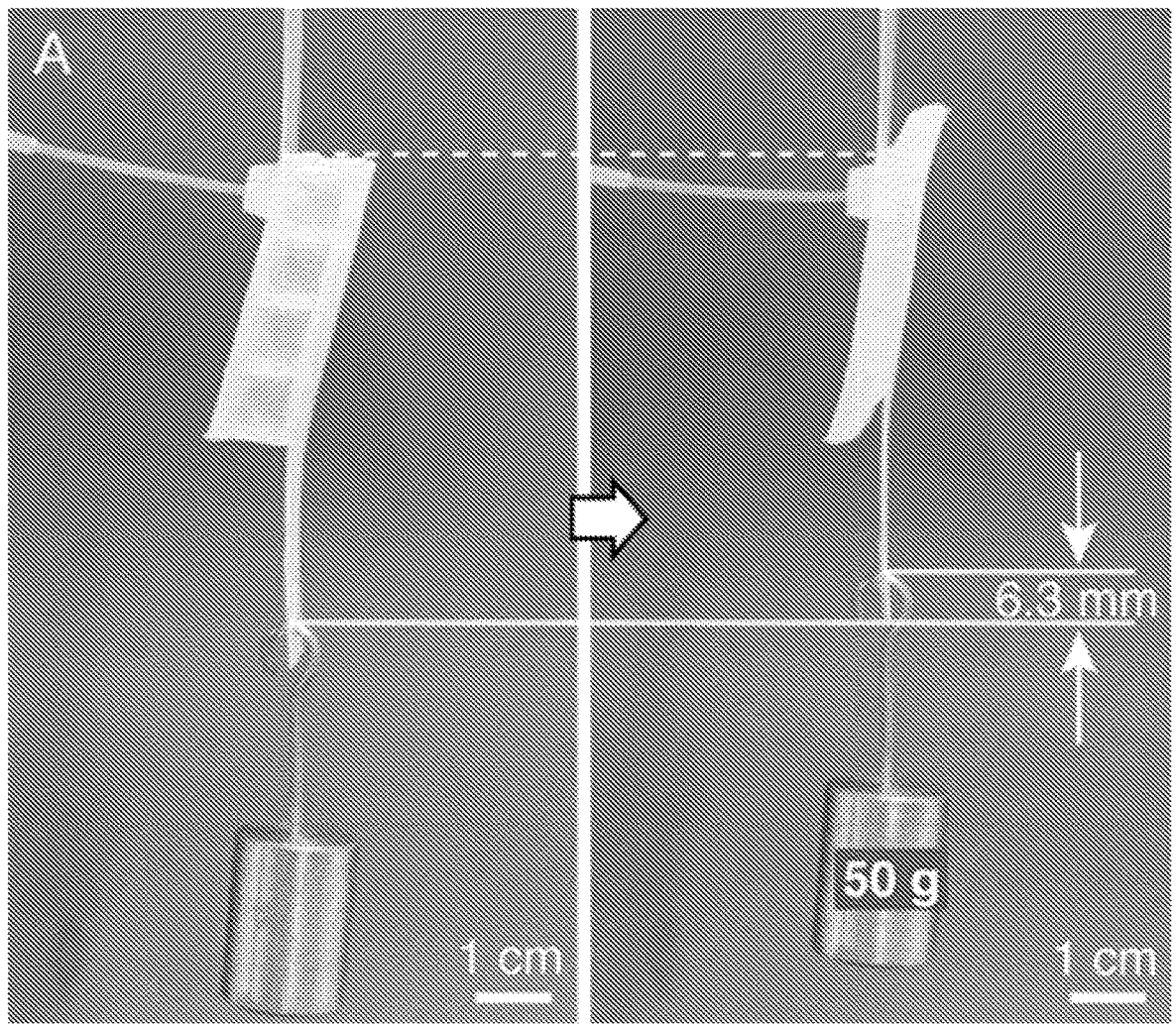
FIG. 3A illustrates a pennate-muscle inspired vacuum actuator (PIVA) made of Ecoflex (E=43 kPa) with five beams lifting a 50-g weight, according to one or more embodiments described herein.
Figure 3B:
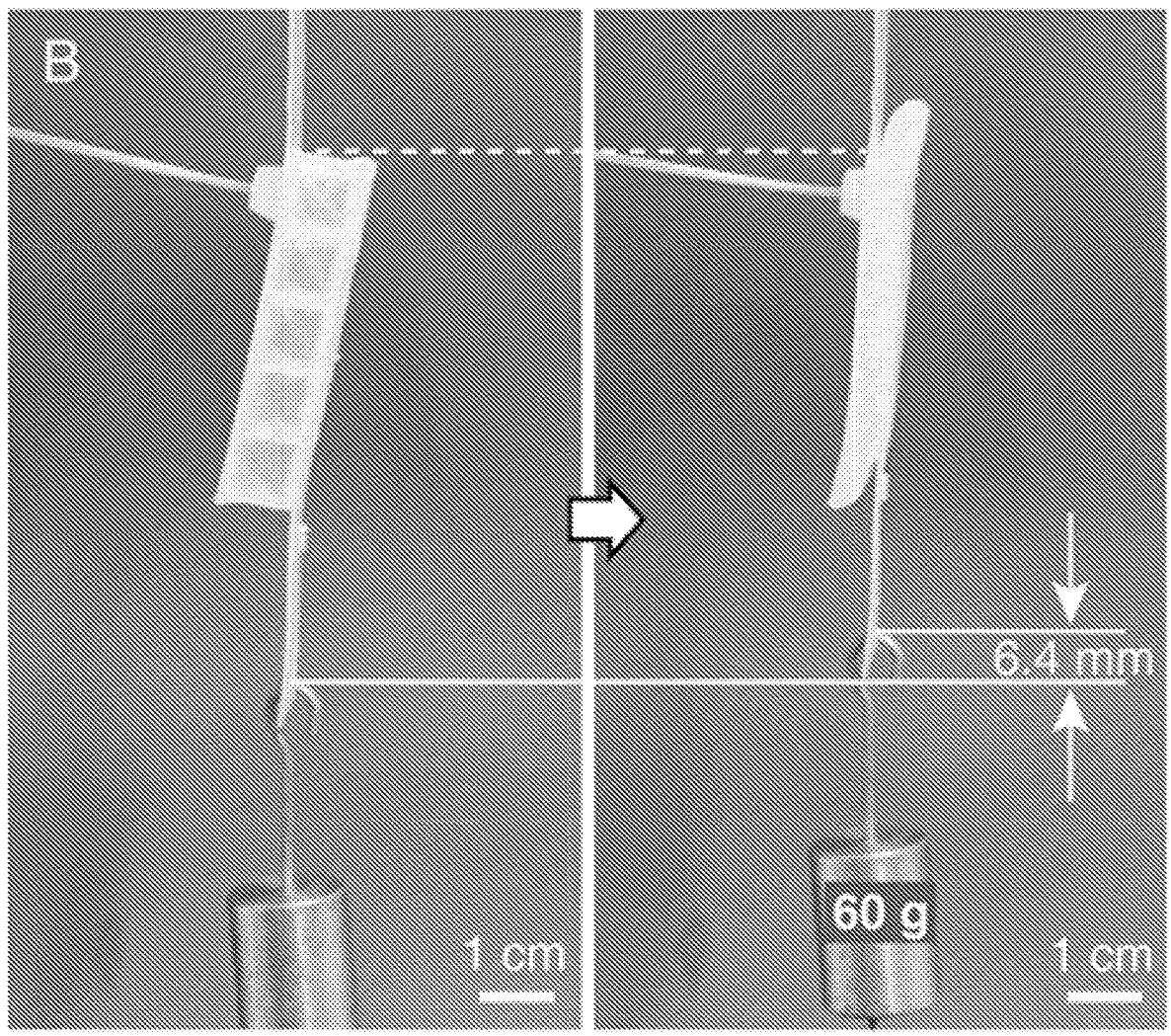
FIG. 3B illustrates a pennate-muscle inspired vacuum actuator (PIVA) made of Ecoflex (E=43 kPa) with six beams lifting a 60-g weight, according to one or more embodiments described herein.
Figure 3C:
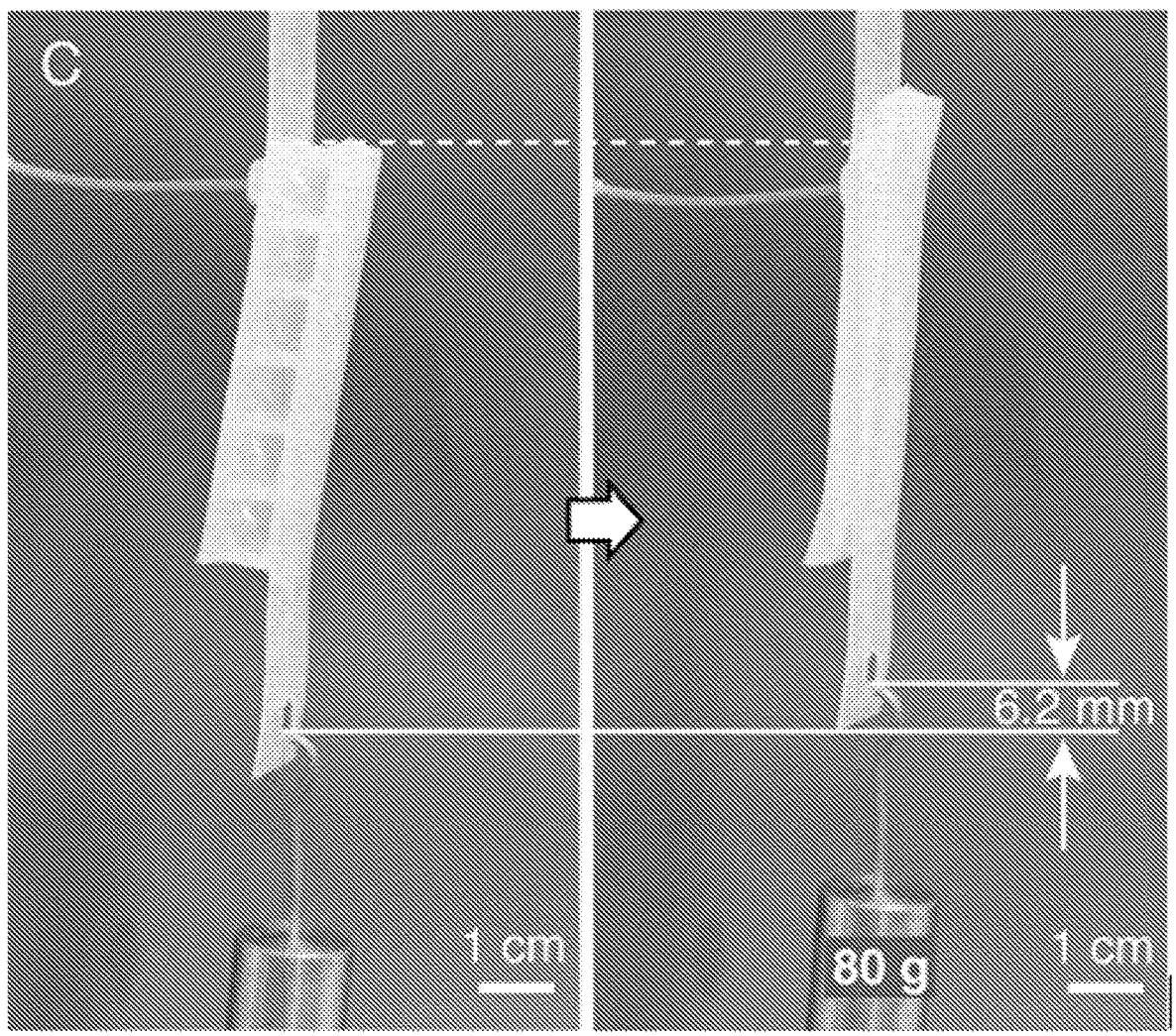
FIG. 3C illustrates a pennate-muscle inspired vacuum actuator (PIVA) made of Ecoflex (E=43 kPa) with seven beams lifting a 80-g weight, according to one or more embodiments described herein.

In certain embodiments, the maximum load a shear-VAM (PIVA) can lift increases with its length or the number of the second structural components. As shown in FIG. 3A, a PIVA made of Ecoflex (E=43 kPa) with five beams can lift a 50-g weight. As shown in FIG. 3B, a shear-VAM (PIVA) of the made of the same material but with six beams can lift a 60-g weight. As shown in FIG. 3C, a shear-VAM (PIVA) of the made of the same material but with seven beams can lift an 80-g weight. In certain embodiments, the actuator as described herein has 2, 3, 4, 5, 6, 7, 8, 10, 20, 50 or more of the second structural components (e.g., beams).

The external fluid inflation or deflation source can be any apparatus that inflates and/or deflates the fluid. Non-limiting examples of the fluid inflation or deflation sources include a gas pump, a gas vacuum, a gas pump and vacuum, a liquid pump, a liquid-suction pump, or a liquid pump and suction pump. In some embodiments, the one or more cells are connected directly to the fluid inflation/deflation source or via a fluid chamber. The use of any fluid, gas or liquid, is contemplated, including air, gas, water, oil, or liquid metal. A non-limiting example of the gas is air. In some specific embodiments, the one or more cells are connected to a gas chamber, which may be connected to the gas inflation/deflation source. In other embodiments, the cell is connected to the gas inflation/deflation source directly. The use of other gases is contemplated.

In certain embodiments, the fluid is gas and the fluid inflation/deflation source is a gas inflation/vacuum source. The external gas inflation source may be a pump, gas cylinder, or balloon. The external vacuum source may be a vacuum pump. Any other gas inflation source and vacuum source known in the art are contemplated.

Thus, in some embodiments, an external deflation source, e.g., vacuum source, is used to induce a negative pressure within the cell, which allows the atmospheric pressure to apply an isotropic compressive force. Pneumatic actuation using air has additional advantages, e.g., that the air it uses is widely available, safe to operate, transfers quickly through tubing (due to its low viscosity), lightweight, and is easily controlled and monitored by regulators, valves, and sensors. In some embodiments, the cells are sealed so that it is topologically closed except for the entrance into the inflation/deflation device or the common air chamber. By connecting the cells and attaching a gas channel, e.g., a tube, to the inflation/deflation device, the cells inside the soft actuator body can be inflated and deflated through pumping air and applying vacuum.

In some embodiments, the shear force actuator comprises more than one cell connected to each other and to the fluid inflation or deflation source, but otherwise isolated from the outside atmosphere. In certain embodiments, the cells are connected to the same external fluid inflation or deflation source. In other embodiments, the cells are connected to a different external fluid inflation or deflation source and can be inflated or deflated (and thus actuated) independent of each other. Thus, the cells can be separate from one another, providing more degrees of freedom of actuation. For example, in certain specific embodiments, two shear force actuators (each with connected cells) can be glued (e.g., with elastomer) side-to-side, thus providing two separately controllable actuating units.

In some embodiments, the soft actuating device further includes one or more hard body portions. In some embodiments, some structural elements may be made from hard materials. Any rigid materials known in the art may be used, as long as they can establish mechanical connection with the soft material used.

In another aspect, a soft actuating device comprising a plurality of the shear force actuator of any one of the embodiments described herein or any combination of the embodiments described herein is described. The cells can be connected to the same external fluid or vacuum source, or at least two of the shear force actuators are connected to different external fluid or vacuum sources capable of being activated independently. As a result, parallel or independent actuation is achieved.

Figure 4A:
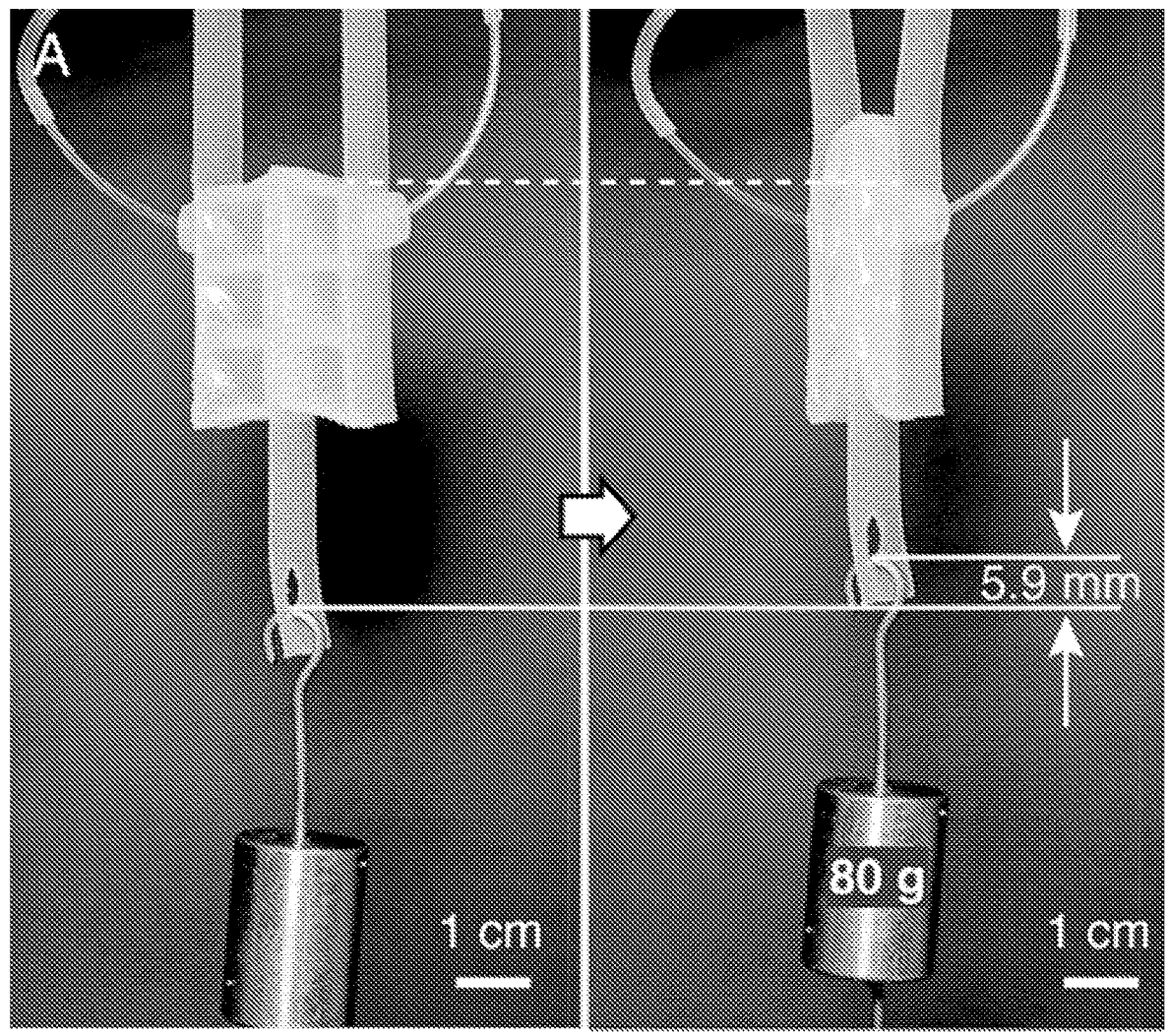
FIG. 4A illustrates two pennate-muscle inspired vacuum actuators (PIVAs or shear-VAMs) working in parallel in a mirror configuration, similar to the mirror arrangements in that of a bipennate muscle, according to one or more embodiments described herein.
Figure 4B:
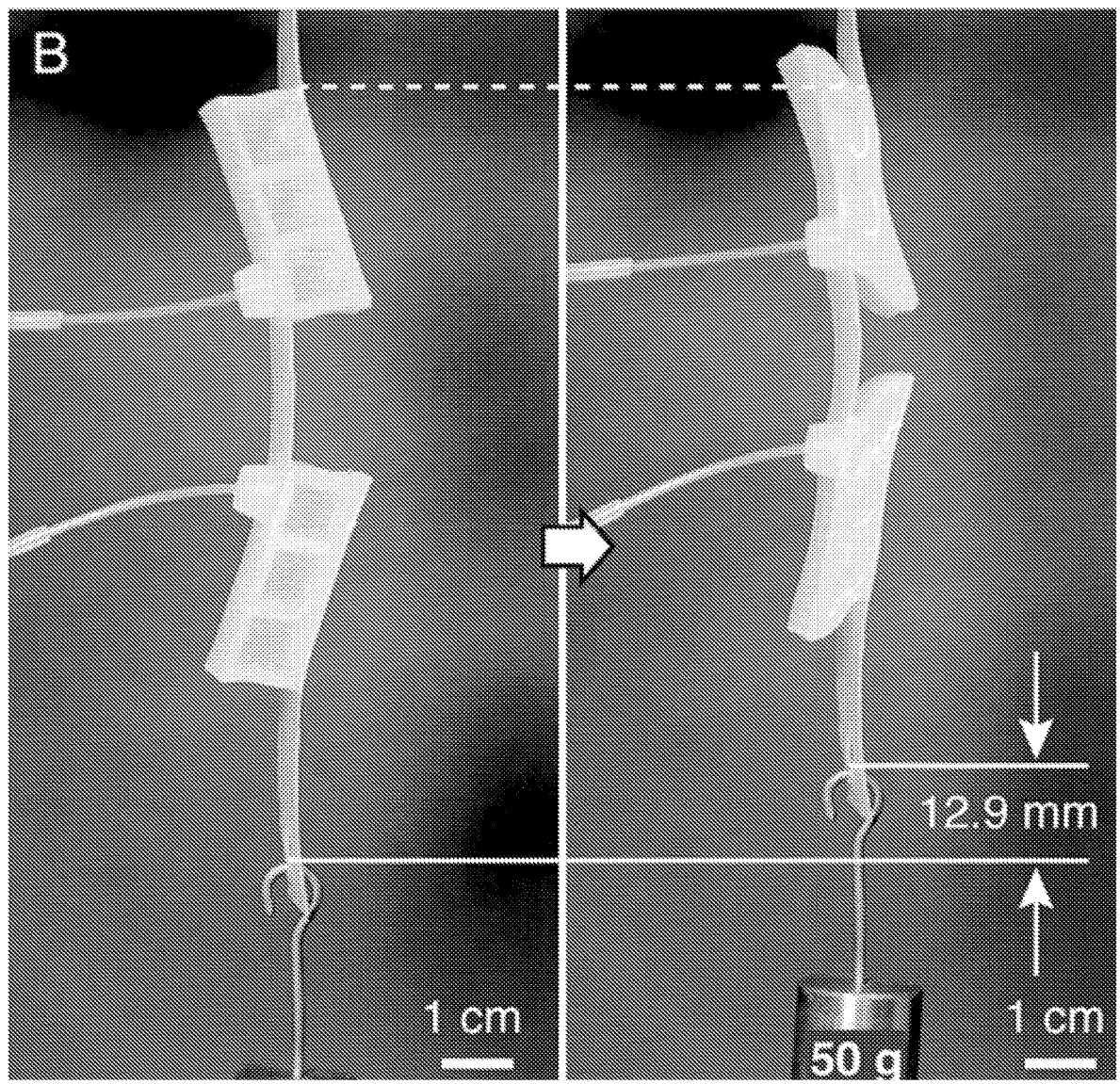
FIG. 4B illustrates two pennate-muscle inspired vacuum actuators (PIVAs or shear-VAMs) working in series generating more lifting height compared to a single PIVA, according to one or more embodiments described herein.

In one or more embodiments, a soft actuating device is made up of two or more soft actuators that share a common first structural component. For example, a single inextensible strip serves as a common wall in integrally-connected soft actuators. FIGS. 4A-4B show multiple PIVAs working in combination. As shown in FIG. 4A, two PIVAs are shown to work in parallel in a mirror configuration, similar to the mirror arrangements in that of a bipennate muscle. This configuration generates more force compared to a single PIVA.

In one or more embodiments, a soft actuating device is made up of two or more soft actuators that are spaced apart along the length of first structural component. For example, a single extensible strip serves as a wall for two or more soft actuators positioned along the length of the strip. As shown in FIG. 4B, two PIVAs are working in series. This configuration generates more lifting height compared to a single PIVA.

In another aspect, a method of actuation is described, including providing the shear force actuator of any one of embodiments described herein; and deflating the cells to cause the cells to collapse to generate a linear force.

Experimental Design of Shear-VAMs (Also Referred to as PIVA)

In some specific embodiments, a design representative of a simple shear-VAM is described, consisting of two flexible but inextensible strips (1.5 mm thick, 17 mm wide, and 10 mm apart) bridged by four tilted parallel elastomeric beams (1.8 mm wide, 8.9 mm long, at 63° angle to the strips, and spaced in 10 mm-intervals along the strips, in FIG. 1c, also referred to as a PIVA). We used a nylon mesh embedded in an elastomer—Ecoflex 00-30 (Young's modulus E=43 kPa), Dragon Skin 10 Slow (E=153 kPa), or Elastosil M4601 (E=520 kPa)—for the inextensible layer. We used the same elastomer in the elastomeric beams in shear-VAMs. The empty spaces in between the beams were converted into enclosed chambers by sealing (front and back) with thin membranes made of the same elastomer (1 mm thick). The final structure comprises a pneumatic structure with several chambers connected to a common source of negative pressure (e.g., vacuum, or pressure less than the ambient pressure). The beams each had an opening in the middle (a 3 mm-wide slit) such that the chambers were pneumatically connected. The chambers were further connected to an external source of vacuum through a piece of tubing that pierces one of the strips. See, FIG. 5 for details of fabrication.

Characterizing the Maximum Force of Actuation of Shear-VAMs

A shear-VAM is similar to a pneumatic or hydraulic piston, in that it works by converting an applied pneumatic pressure $\Delta P$ to an output force F. As we apply an increasing difference of pressure $\Delta P$ (as defined in Equation 1) between that of the atmosphere external to the shear-VAM ($P_{ext}$), and that of the partial vacuum inside it ($P_{int}$), its void chambers deflate, and the two inextensible strips translate relative to each other (as shown in FIG. 1D).

$$\Delta P = P_{ext} - P_{int} \quad (1)$$

The two inextensible strips move until, at a critical difference of pressure $\Delta P_{crit}$, the void chambers collapse completely (or as completely as they can within the limits of the design) and bring the actuator to a stop. The actuation of a shear-VAM results in a decrease in its length $\Delta h$ (also indicated in FIG. 1D). We defined this change in length $\Delta h$—effectively the relative distance of translation between the two inextensible strips—to be the distance of actuation of a shear-VAM. The actuation of a shear-VAM also applies a force F, as indicated in FIG. 1B and defined in Equation 2, where m is the mass of a test object, and a is the acceleration of that object. We defined this force—the force that lifts and accelerates a load—to be the force of actuation of a shear-VAM.

$$F = mg + ma \quad (2)$$

Figure 6A:
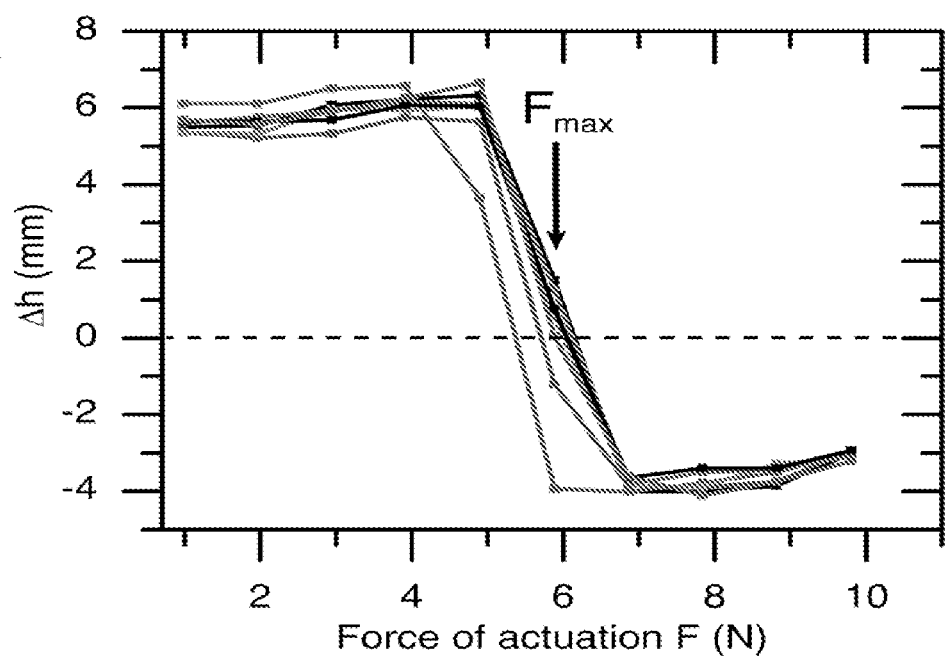
FIGS. 6A-6B show the characterizing the maximum force of actuation of shear-VAMs.
Figure 6B:
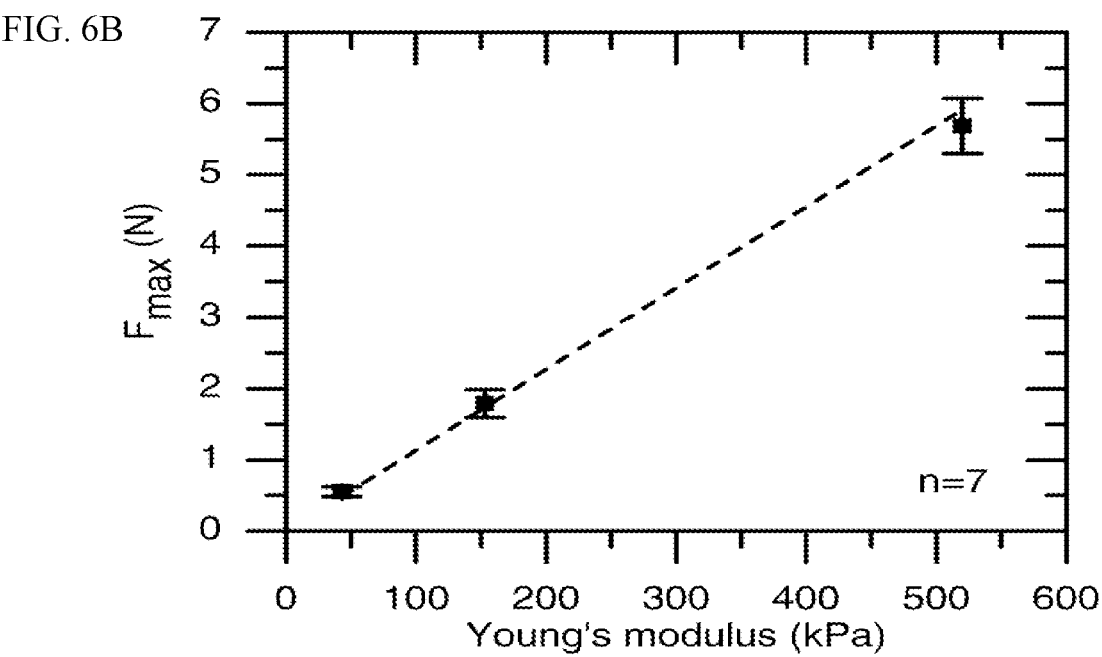
Figure 7A:
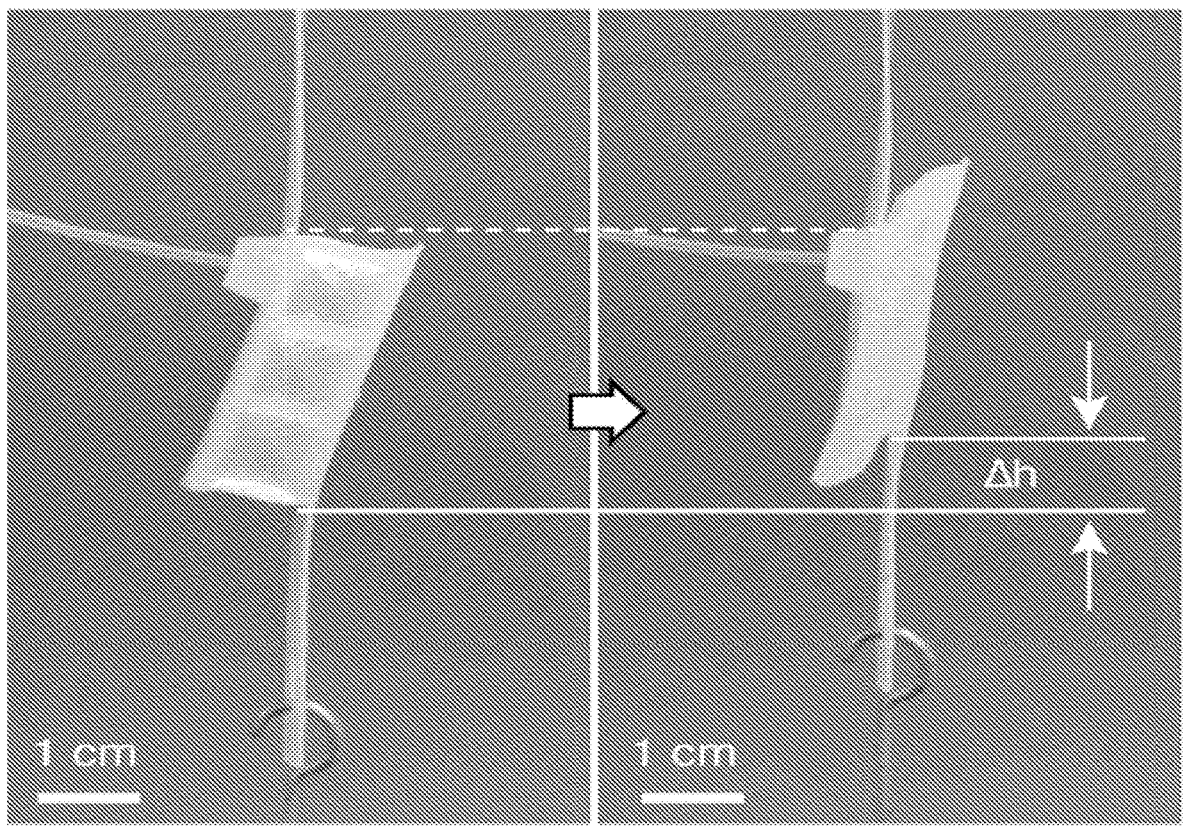
FIGS. 7A-7B show a shear-VAM contracts or extends on actuation depending on the load.
Figure 7B:
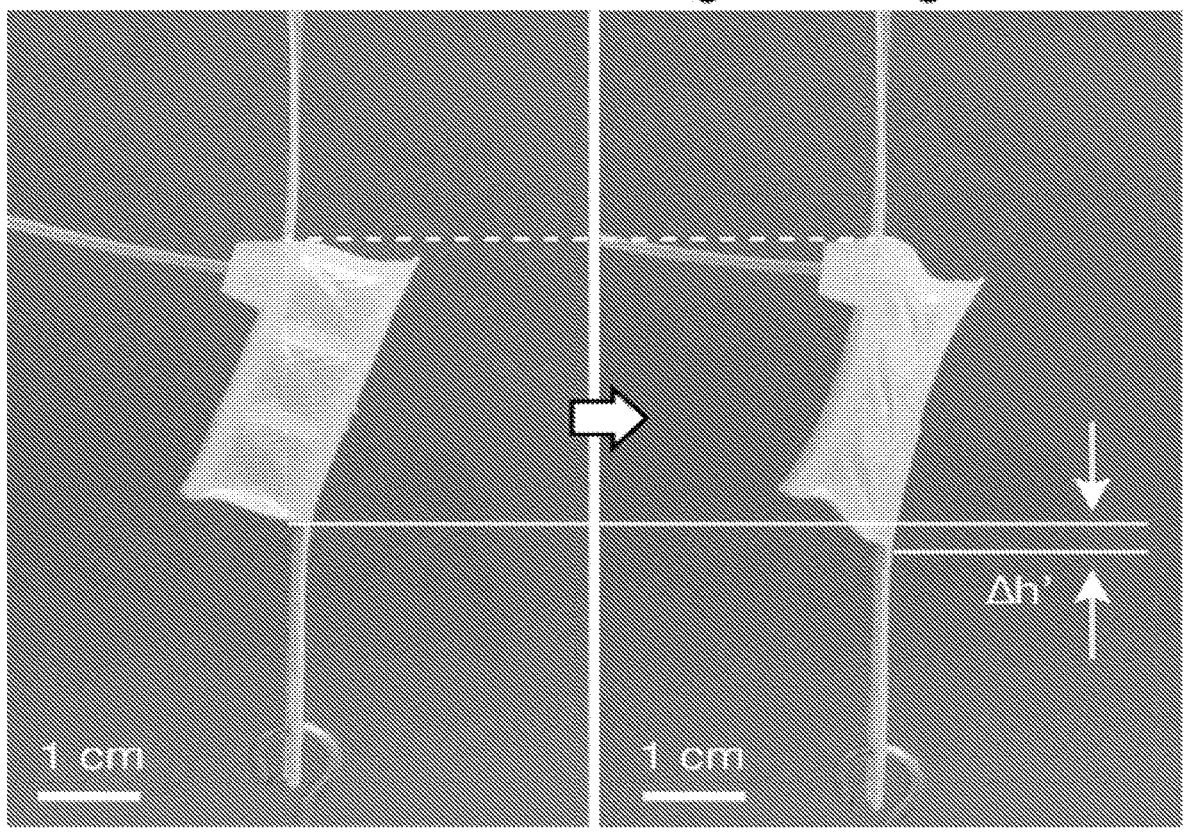

The distance of actuation $\Delta h$ (upon application of a difference of pressure $\Delta P > \Delta P_{crit}$) is determined primarily by the geometry of the shear-VAM. FIG. 6A shows that this distance $\Delta h$ stays roughly constant when various loading forces F (in N, given by a hanging weight) are applied to the shear-VAM while it actuates, as long as the loading force is less than a certain maximum value $F_{max}$. We define $F_{max}$ to be the maximum force a shear-VAM of this particular design can generate. For a load F greater than $F_{max}$, the beams in the shear-VAM will tilt in the opposite direction when the pressure $\Delta P$ is increased. In other words, the shear-VAM lifts the weight for a distance of $\Delta h$ while $F < F_{max}$ (i.e., produces a contraction), and it lowers the weight for a distance of $\Delta h'$ while $F > F_{max}$ (i.e., produces an elongation). FIG. 6B shows the relationship between the maximum force of actuation $F_{max}$ of shear-VAMs (in N) and the Young's Modulus E (in kPa) of the elastomer used in fabricating the shear-VAMs. FIGS. 7A-7B demonstrate this effect. The distance of elongation $\Delta h'$ is again roughly constant under various constant loads F greater than $F_{max}$, as $\Delta h'$ is also determined primarily by the geometry of the shear-VAM. FIG. 7a) shows the shear-VAM lifts the weight for a distance of $\Delta h$ upon actuation while $F < F_{max}$. FIG. 7B shows the shear-VAM lowers the weight for a distance of $\Delta h'$ upon actuation while $F > F_{max}$. The difference of pressure applied is $\Delta P = 90$ kPa.

The value of $F_{max}$ is dependent on various characteristics (geometry and materials parameters) of the actuator. For example, for shear-VAMs that have the same geometry, ones that are stiffer (i.e., made of elastomers with higher Young's modulus) generate a higher force upon actuation. FIG. 6B shows that the maximum force of actuation $F_{max}$ (in N) of a shear-VAM is proportional to the Young's modulus E (in Pa) of the material of which it is fabricated (Equation 3):

$$F_{max} = kEL^2 \quad (3)$$

Where L is the length scale (in this case the length) of the shear-VAM, and k is a dimensionless constant. FIGS. 2A-2B show that PIVAs (also referred to as shear-VAMs) with indistinguishable geometries, but made in different materials, lift different weights.

This linear relationship (Equation 3) is confirmed theoretically though dimensional considerations (a detailed theoretical analysis is provided below). This scaling property (Equation 3) allows one to construct shear-VAMs capable of generating a high force simply by choosing a stiff elastomer during fabrication.

Characterizing the Thermodynamic Efficiency of shear-VAMs.

Figure 8:
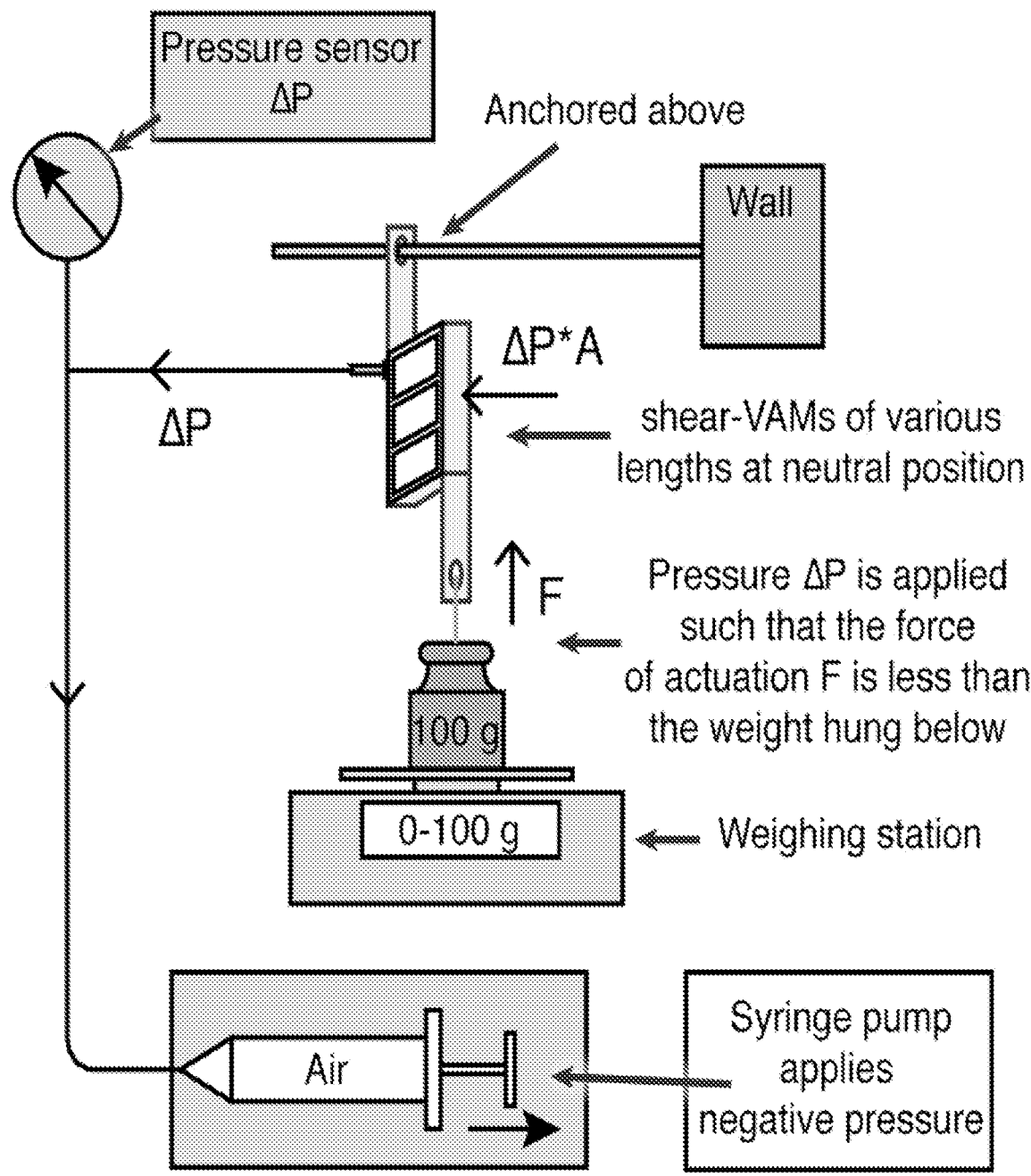
FIG. 8 shows a schematic diagram for the testing setup that measures relationship between the force of actuation F of shear-VAMs and the difference of pressure $\Delta P$ applied across the inside and outside of the shear-VAMs.

The thermodynamic efficiency of transduction of the pressure-volume work required to actuate shear-VAM into mechanical (force×distance) work (e.g., lifting a weight) is limited by the work required to compress the elastomer. By comparison, the loss of energy due to hysteresis is small (details are provided below and in FIG. 8). As shown in FIG. 8, the bottom end of the shear-VAM is tied to a weight placed on a scale to measure the force of actuation of the shear-VAM. The forces did not exceed the weight and thus, the weight did not lift off the scale. The scale together with the weight acts as a strain gauge to measure the force of actuation F of the shear-VAMs. Our experimental data yield a thermodynamic efficiency of 35% for a distance of actuation of ~4.7 mm at 200 g loading for the shear-VAM shown in FIG. 1b). In comparison, the corresponding value of a human skeletal muscle is ~40%. The energy stored in the deformed, elastomeric components (which is not converted into useful mechanical work and thus reduces the thermodynamic efficiency for a single, unidirectional motion) can, in principle, be at least partially recovered during unloading. Another similar VAM—a linear VAM—has a similar potential for recovery of energy. This method of storing and recovering energy of soft actuators has been reported in a number of designs.

Characterizing the Mechanical Advantage of Shear-VAMs.

We define the geometrical parameters that characterize a shear-VAM (FIG. 9a)), where: L is the length of the elastomeric body of the actuator (i.e. the long dimension of the parallelepiped), a is the length of the tilted beams, b is the width of the actuator (i.e. the third dimension of the parallelepiped), $\alpha$ is the angle between the strips and the beams, and $A = L \times b$ is the "lateral area" of the shear-VAM (the shaded area in FIG. 9A). The force of actuation is approximately given by Equation 4 (the description below includes a theoretical derivation).

$$F = \eta(\alpha) A \Delta P / \tan(\alpha), \quad (4)$$

where $\eta(\alpha)$ is the thermodynamic efficiency of the shear-VAM for an infinitesimal movement near angle $\alpha$. This value is approximately equal to the total thermodynamic efficiency of the shear-VAM $\eta$.

Figures 9A, 9B, 9C:
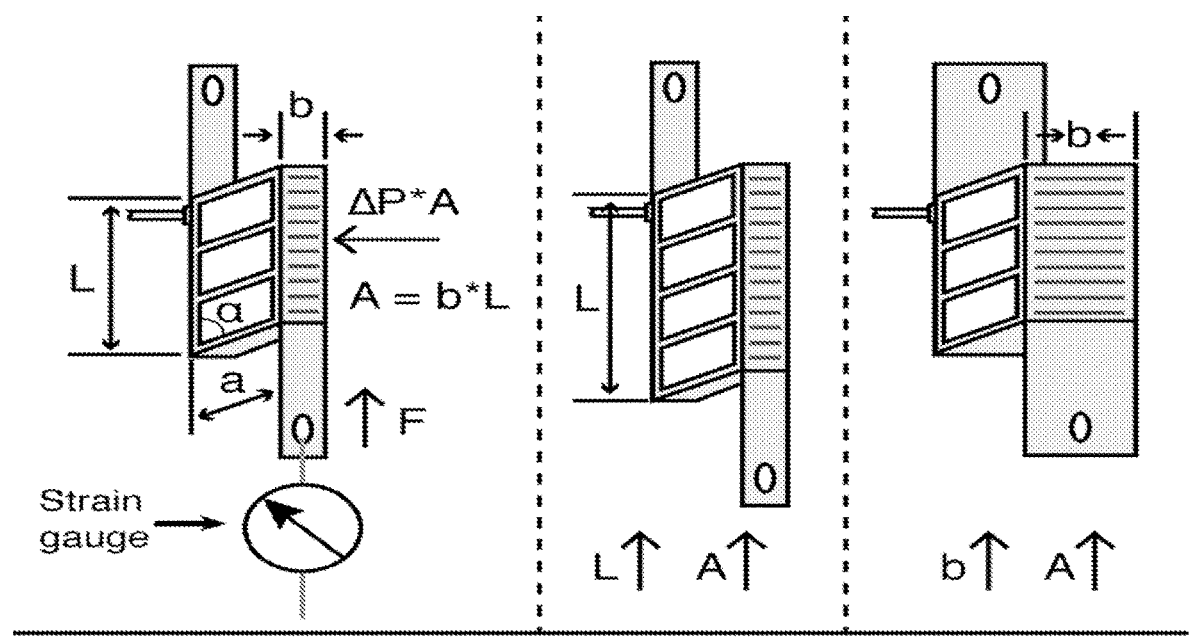
FIGS. 9A-9E show the characterizing the mechanical advantage of shear-VAMs.

Equation 4 indicates that we can increase the force of actuation of a shear-VAM by increasing the lateral area of the shear-VAM $A = Lb$ (FIG. 9A). Assuming the pneumatic source has a fixed working area of $A_0$, it generates a driving force of $F_{in} = A_0 \Delta P$. The shear-VAM demonstrates a net mechanical advantage (MA) given by Equation 5.

$$MA = F/F_{in} = \eta A / (A_0 \tan(\alpha)) \quad (5)$$

We note that the mechanical advantage of a shear-VAM can be, in principle, increased indefinitely as we increase the lateral area A (although the MA is, of course, limited by the tensile strength of the strips). FIGS. 9B-9C illustrate two cases where we increase either the length L or the width b to increase the lateral area A, and consequently, boost the force of actuation F.

In particular, increasing the length L allows a shear-VAM to increase its force of actuation F without increasing the apparent cross-sectional area $ba \sin(\alpha)$. This feature is useful, as it allows these actuators to have a "mechanical advantage" also in the sense of pressure ($MA_p$), defined as the ratio of the pressure that performs useful work to the pressure that is applied (Equation 6).

$$MA_p = P_{out}/P_{in} = \eta L/(a \sin(\alpha)) \quad (6)$$

where $P_{out} = F/(ba \sin(\alpha))$, and $P_{in} = \Delta P$.

Figure 9D:
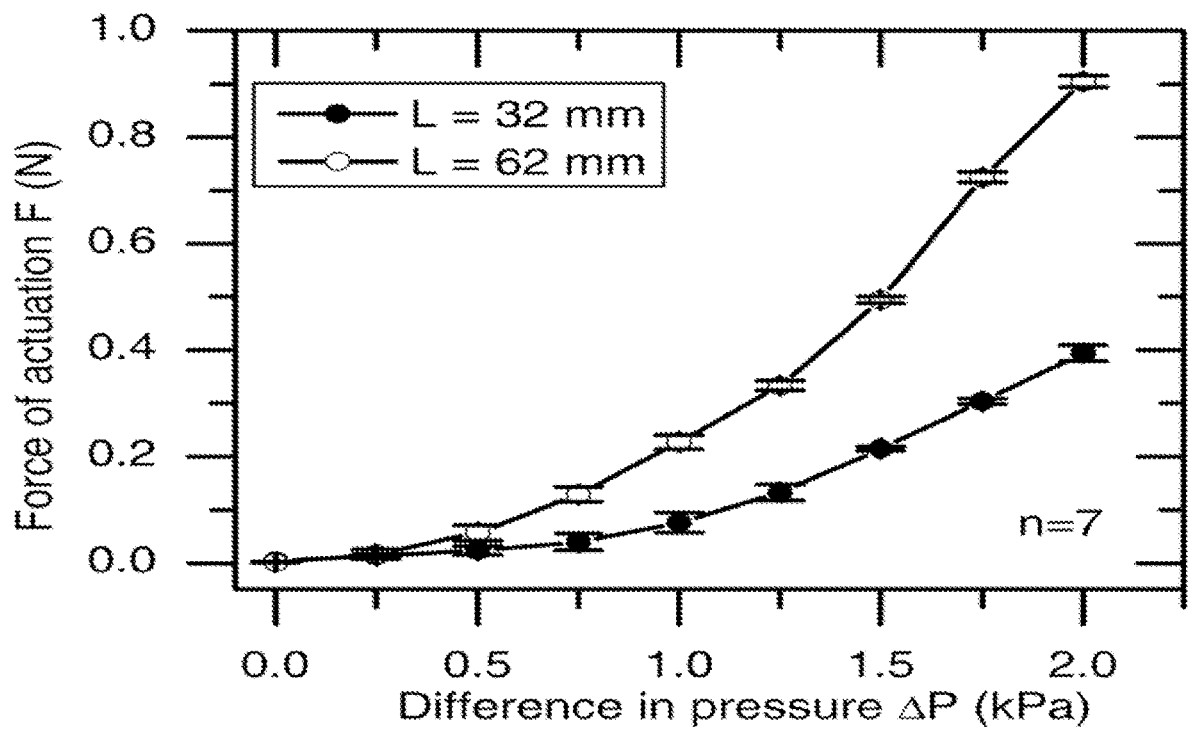
Figure 9E:
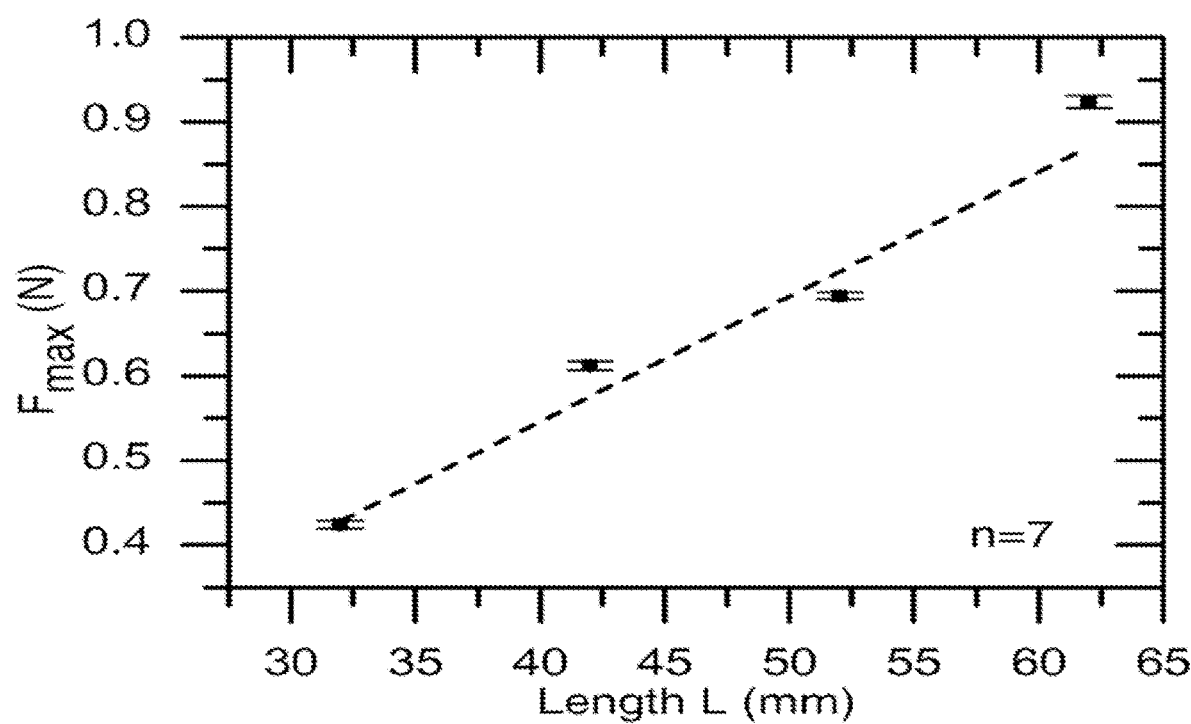
Figure 10:
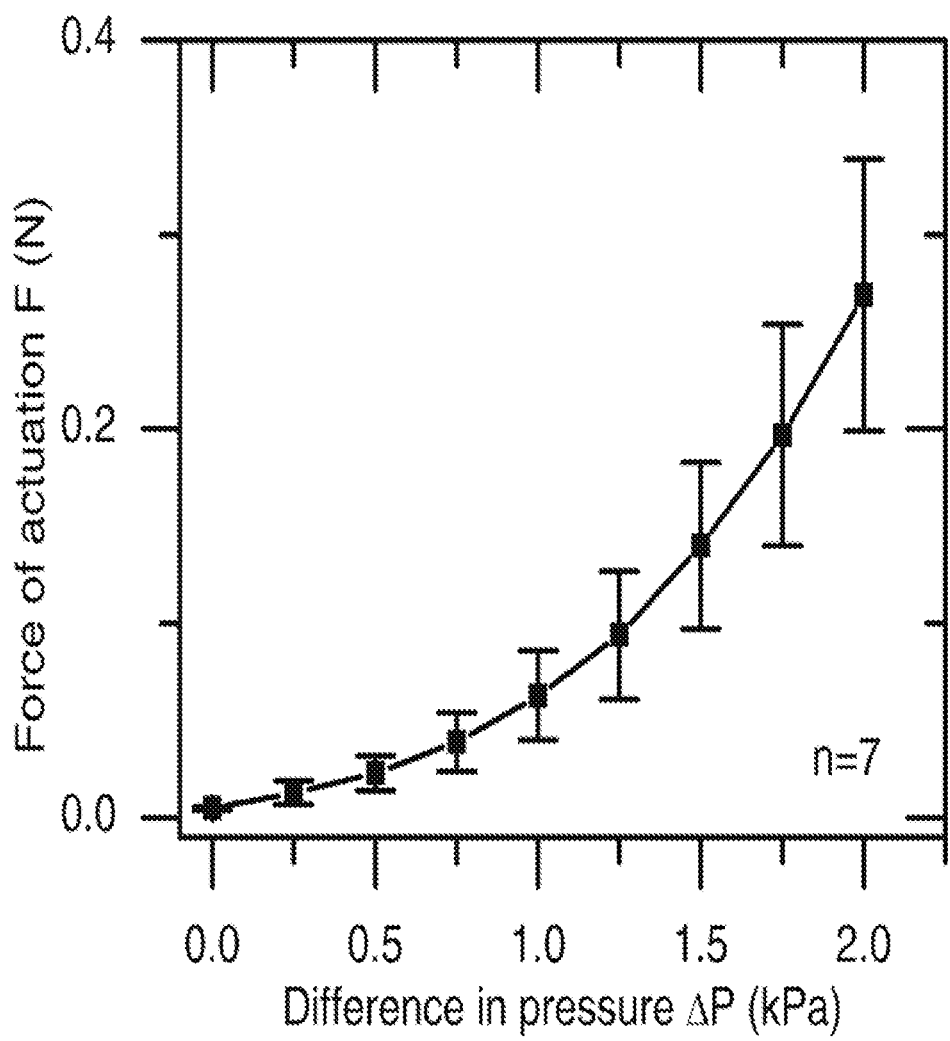
FIG. 10 shows the force of actuation F of seven different shear-VAMs of length L=32 mm (connected to a fixed strain gauge) vs. the difference of pressure $\Delta P$ (in kPa) applied across the inside and outside of the shear-VAMs.

FIG. 9D shows the relationship between the force of actuation F of shear-VAMs of two different lengths L=62 mm and 32 mm (each connected to a fixed strain gauge), and the difference of pressure $\Delta P$ (in kPa) applied across the inside and outside (the ambient atmosphere) of the void chambers of these shear-VAMs (see the SI and Figure S6 for details of this measurement). At the same $\Delta P$, the curves show a near doubling of force of actuation F, when the length L is doubled—consistent with Equation 4. FIG. 9E shows that the maximum force of actuation of shear-VAMs $F_{max}$ also increases with their length L, consistent with Equation 4. The plot verifies that the relationship is linear. Error bars in FIGS. 9D-9E were measured from seven replicate measurements of the same sample (standard deviation of measurement on different devices are larger, as shown in FIG. 10, but can in principle be greatly reduced in machine-made devices as opposed to handmade ones). Specifically, FIG. 10 shows the force of actuation F of seven different shear-VAMs of length L=32 mm (connected to a fixed strain gauge) vs. the difference of pressure $\Delta P$ (in kPa) applied across the inside and outside of the shear-VAMs.

Parallel Actuation and Stackability of the Shear-VAMs.

Multiple shear-VAM units can be positioned in parallel or in series and actuated together to generate more force or more distance of actuation (see FIGS. 4A-4B). FIG. 4A shows two shear-VAMs working in parallel in a mirror configuration. This configuration generates about twice as much force (~2F) as a single shear-VAM of the same length L, but has about the same distance of actuation (~$\Delta h$). FIG. 4b) shows two shear-VAMs working in series. This configuration has about twice the distance of actuation (~2$\Delta h$) as a single shear-VAM of the same geometry, but generates about the same force (~F). These force or distance scaling relationships are universal to parallelizing or stacking of any linear actuator. Shear-VAMs, in particular, are naturally fit for parallelization, as their lateral areas remain flat during actuation (as shown in FIG. 4A); the same is not true for other pneumatic linear actuators such as McKibben actuators).

Using Shear-VAMs in Robots That Locomote.

Figure 11A:
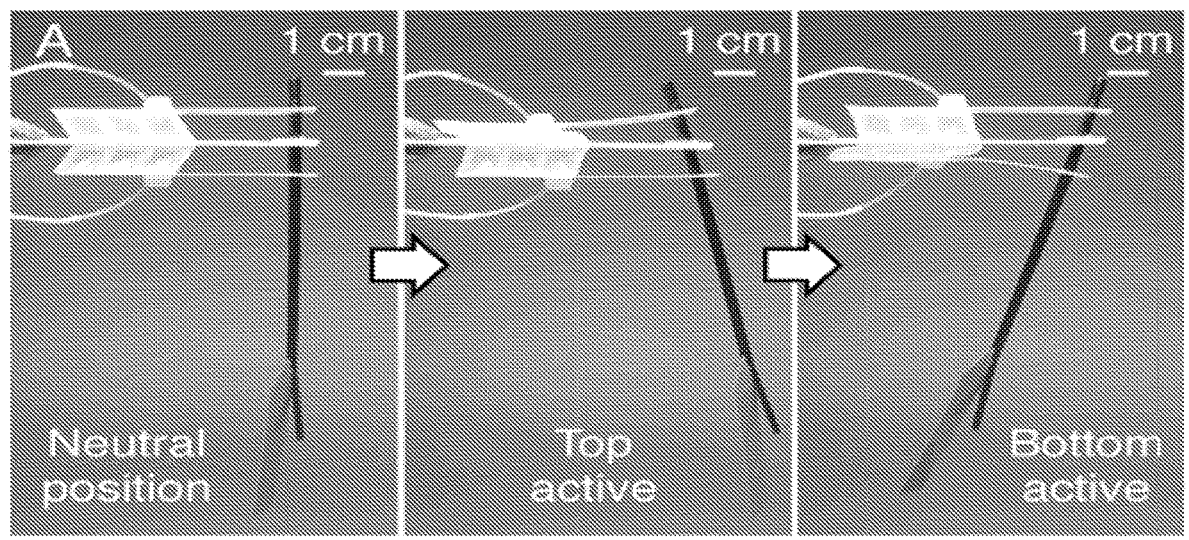
FIGS. 11A-11B show soft robot actuated with shear-VAMs.
Figure 11B:
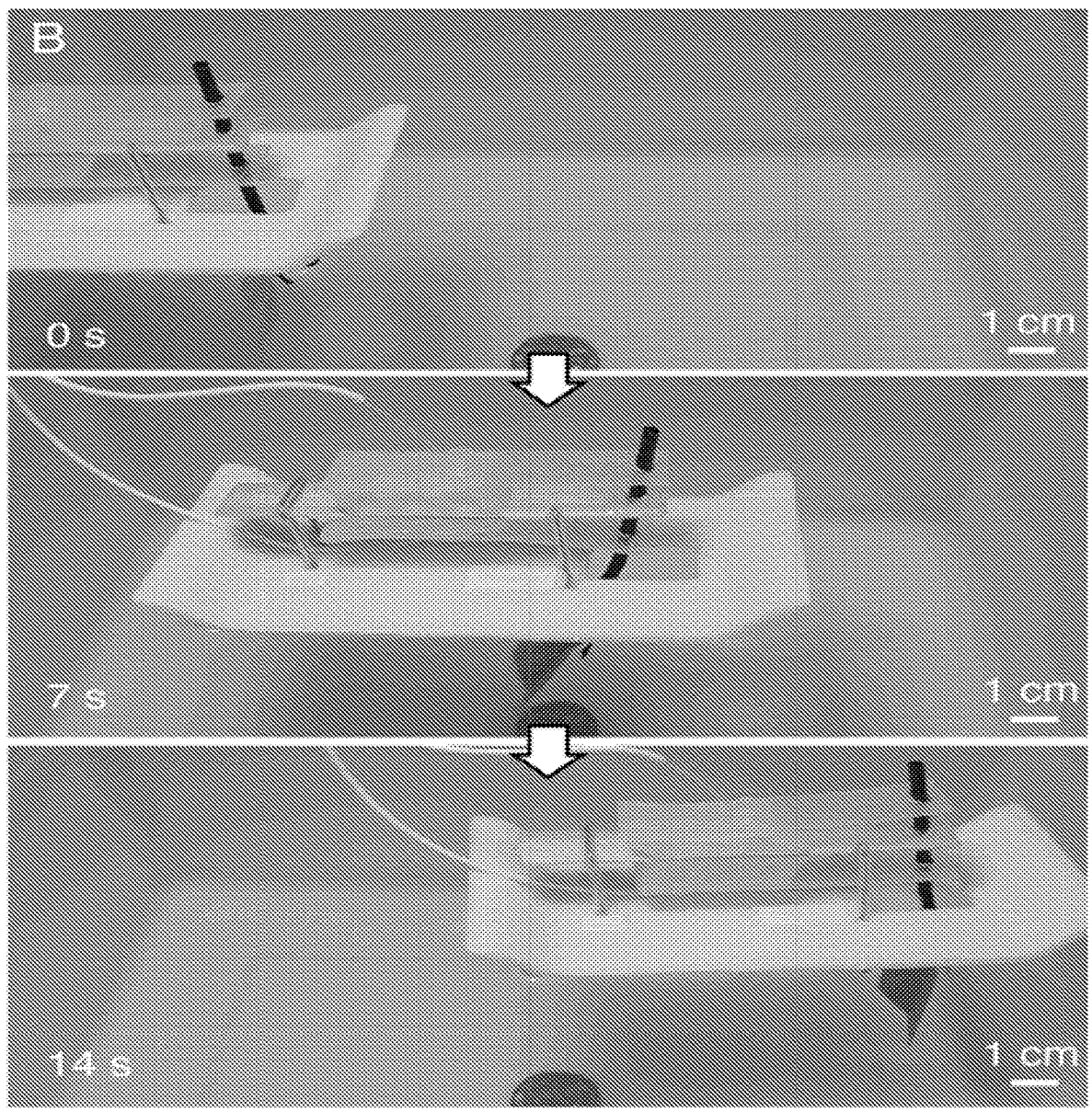

The agonist-antagonist arrangement is useful in the muscle of animals in enabling more effective movements. Since shear-VAMs resemble biological muscle in that they are soft linear actuators, this arrangement can be borrowed in making devices with shear-VAMs that move or locomote. FIGS. 11A-11B show a swimming device that uses a pair of shear-VAMs in an agonist-antagonist arrangement to drive its paddle. The paddle moves either forward or backward when the corresponding shear-VAMs actuate and pull the lever that is connected to the paddle. The paddle can pivot around its connection backwards but not forward—this design helps to generate a hysteresis that is required to propel the swimmer forward in water.

In certain embodiments, shear-VAMs or PIVAs described herein have three characteristics that are useful for making soft machines: i) they provide a tunable mechanical advantage; ii) they can be easily used in series or in parallel; and iii) they contract rather than expand in volume on actuation. Shear-VAMs and other soft pneumatic actuators are useful in supplementing more familiar hard machines with the following advantages: i) increased safety in use around humans or animals, and non-damaging interactions with delicate objects; ii) low cost of fabrication; and iii) light weight and low density (mostly air, the elastomers we use have densities around ~1 g/cm$^3$).

In certain embodiments, a shear-VAM or PIVA described herein is a soft linear actuator that works by converting the pneumatic pressure applied perpendicular to its inextensible lateral surfaces to a force parallel to them via tilted elastomeric beams. It provides a mechanical advantage in terms of (that is, it can magnify) both force and pressure relative to the input. It does so by increasing its length (for both force and pressure) or width (for only force). The design of shear-VAM provides a new tool for making biomimetic and/or functional soft machines. Shear-VAMs could, in particular, be useful for generating high forces or generating reasonable forces with a small input pressure in a soft structure.

Soft linear actuators as described herein, e.g., PIVAs or Shear-VAMs, are useful for making collaborative machines (e.g., machines that interact safely with people in continuous, transitory, intentional, and incidental contact) and in designing biomimetic robots based on animals over a range of levels of evolutionary development. This study demonstrates a new type of soft linear actuator that uses negative pressure (vacuum) for its actuation. This actuator also acts as a device designed to generate a tunable mechanical advantage—the ratio of the force that performs useful work to the force that is applied—in soft materials. It expands the capabilities of soft robots and machines, and in particular, overcomes one of the limitations of current soft pneumatic actuators—that is, the force they apply is limited by the pressure used to actuate them.

Characterizations of Shear-VAMs (Also Referred to as PIVA)

Here we discuss the relationship between the actuation stress of a PIVA and its various physical parameters. Before we consider differences in geometry, we first note that comparing two PIVAs, made of elastomers with different Young's modulus, but their geometries being otherwise the same, the stiffer one can generate a higher force upon actuation. FIGS. 2A-2B show that PIVA fabricated from a stiffer elastomer can lift a heavier weight. The maximum weight a PIVA made of Ecoflex (Young's modulus E=43 kPa) with four beams (with dimensions specified above) can lift is ~40 g, while a PIVA of the same geometry but made of Elastosil (E=520 kPa), can lift a maximum load of ~400 g. PIVAs exert greater force when fabricated in stiffer elastomers—an approximately ten-fold increase in the modulus of the material resulted in an approximately ten-fold increase in maximum load. FIGS. 2A-2B show that the Young's modulus of the elastomeric material used to fabricate a PIVA is approximately proportional to the maximum load it can lift. This linear relationship is theoretically confirmed though dimensional considerations (detailed theoretical analysis is shown below). This scaling property allows one to construct PIVAs capable of generating high force simply by choosing a stiffer elastomer in fabrication. This scaling law holds as long as the inextensible layers are made of material that is sufficiently strong that they do not break over the range of forces we apply. The tensile strength of the inextensible strips ultimately limit the force that can be generated by a PIVA.

For a PIVA made of a material of known modulus, several geometric parameters affect the force it can produce. When actuated, a horizontal force in the actuator T (in Newtons) is initially generated by a difference in pressure, $\Delta P$, between the external ambient pressure Pext (typically ~1 atm≈100 kPa) and the partial vacuum inside the pneumatic chambers Pint, as shown in equation 1a and 2a, where A (in m$^2$) is the side-surface area of either of the two strips where there is a difference in pressure ΔP applied across it (this area is the same of the two strips due to the actuator having C2 symmetry). The actuator then converts this horizontal force T into a vertical force G (in Newtons) through the leverage of the oblique beams to counteract the load. This force conversion is illustrated in the force diagram in FIG. 1c, where F is the force sustained by the beams, and α is the angle between elastomeric beams and the inextensible strips. In a quasi-static condition, the relationship between these three forces is expressed in equation 3a.

$$T=\Delta P \cdot A \tag{1a}$$

$$\Delta P=P_{ext}-P_{int} \tag{2a}$$

$$G=\cot(\alpha) \cdot T=\sin(\alpha) \cdot F \tag{3a}$$

From equation 3a, we deduce that a necessary and sufficient condition on whether a PIVA can lift a weight G (in Newtons) is summarized in equations 4a-6a, where $\alpha_0=63.4°$ is the angle between elastomeric beams and the inextensible strips before the load G is applied, $\alpha_1$ is the angle between elastomeric beams and the inextensible strips after the load G is applied, and $F_{max}$ is the maximum force the beams in the PIVA can sustain before collapsing.

$$G<\cot(\alpha_1) \cdot \Delta P \cdot A \tag{4a}$$

$$G \leq F_{max} \tag{5a}$$

$$\alpha_0<\alpha_1<90° \tag{6a}$$

These relationships (equations 4a-6a) show three fundamental constraints that limit the force that can be generated by a PIVA: i) The pressure difference across the inextensible strip $\Delta P$ (limited by the atmospheric pressure) multiplied by the area on the side of the PIVA A must amount to a force sufficient to overcome the load G at the initial angle $\alpha_1$; ii) the maximum force $F_{max}$ the beams in PIVA can sustain (limited by the stiffness, thickness, and spacing of the beams). We note that $F_{max}$ is proportional to the length of the actuator that the stiffness, the thickness, and the spacing of the beams are constant (as a taller strip amount to proportionally more beams provided the spacing of beams is constant). One can minimize this limitation by fabricating the beams out of very stiff material. In principle, the beams can be made of hard materials rather than elastomers to circumvent this limitation, as long as the bases of the beams are allowed to rotate relative to the inextensible strips; and iii) the load must not be so high that the initial angle between the beams and the inextensible strips under load $\alpha_1$ are higher than 90° (the PIVA will otherwise not be able to sustain a positive load, according to equation 3a). The angle $\alpha_1$ in this particular design of PIVA largely depends on the tension provided by the membrane that seals the pneumatic chambers. The stiffer the membrane, or the longer the dimension of the membrane along the strip, the smaller the difference between $\alpha_1$ and $\alpha_0$. Notably, one can proportionally increase the load G and the dimension of the membrane along the strip proportionally (that is, increasing the length of the actuator) without changing the angle $\alpha_1$ (as the membrane per unit length of the actuator is still bearing the same weight, despite the increase in total load G). In optimizing the strength of PIVA, this limitation can be entirely avoided by using hard beams with joints to replace the soft beams, while putting an angle-limiting mechanism on the hard joints. Using this method, in principle, one can enforce the relationship: $\alpha_0=\alpha_1<90°$.

By observing these above limitations to the force a PIVA can generate, we notice that the load G a PIVA can lift can be increased if one proportionally increases the length of the actuator, provided that the geometry of individual beams, the vertical spacing of the beams, and the differential pressure applied to PIVA $\Delta P$ do not change. This feature of PIVA is very similar to how pennate muscle increases its strength (relative to a muscle with parallel fiber arrangement) by stacking obliquely angled muscle fibers along its direction of actuation (although the direction of slanting of beams in a PIVA is the opposite of that of fibers in a pennate muscle). This feature of PIVA is demonstrated in FIGS. 3A-3C, where we show that the maximum load a PIVA can lift increases with its length and number of cells. In some embodiments, there is an approximately a linear relationship between the maximum load a PIVA can lift and the length of the PIVA. This scaling relationship provides a method to increase the load a PIVA can lift without adding any cross-sectional area. The drawback of this method of increasing actuation stress is that it also increases the total length of the actuator without increasing the actuation distance, resulting in a smaller actuation strain. When choosing geometries of PIVA for different applications, one can either choose long or short PIVA in favor of a higher actuation stress or a higher actuation strain.

The class of soft pneumatic actuators that PIVAs represent—actuators that combine vacuum and buckling of elastomeric beams as a mechanism for actuation—has six characteristics that are useful for making soft machines: i) no expansion in volume on contraction; ii) safety in use around humans or animals, and non-destructive interactions with delicate objects; iii) low cost of fabrication; iv) lightweight and low-density (mostly air, elastomers we use have densities around ~1 g/cm$^3$); v) performance (stress, strain, speed, thermodynamic efficiency) similar to that of natural muscles; and vi) long lifetime.

PIVAs are shear force actuators of almost arbitrarily high-stress output, while the input pneumatic pressure is limited (the stress output is only limited by the tensile strength of the inextensible layers, which can be made of very strong material such as carbon fibers). PIVAs also demonstrate a simple way of generating soft linear motions that can be tuned to fit different requirements of mechanical performance of different applications, similar to how humans and animals use the same muscle fibers, but different fiber arrangements, to adapt to performance requirements at different parts of their bodies. This tunability of PIVAs may prove useful to construction of robots that has similar body plans to that of humans or animals.

Fabrication of Shear-VAMs (Also Referred to as PIVAs).

Figure 5:
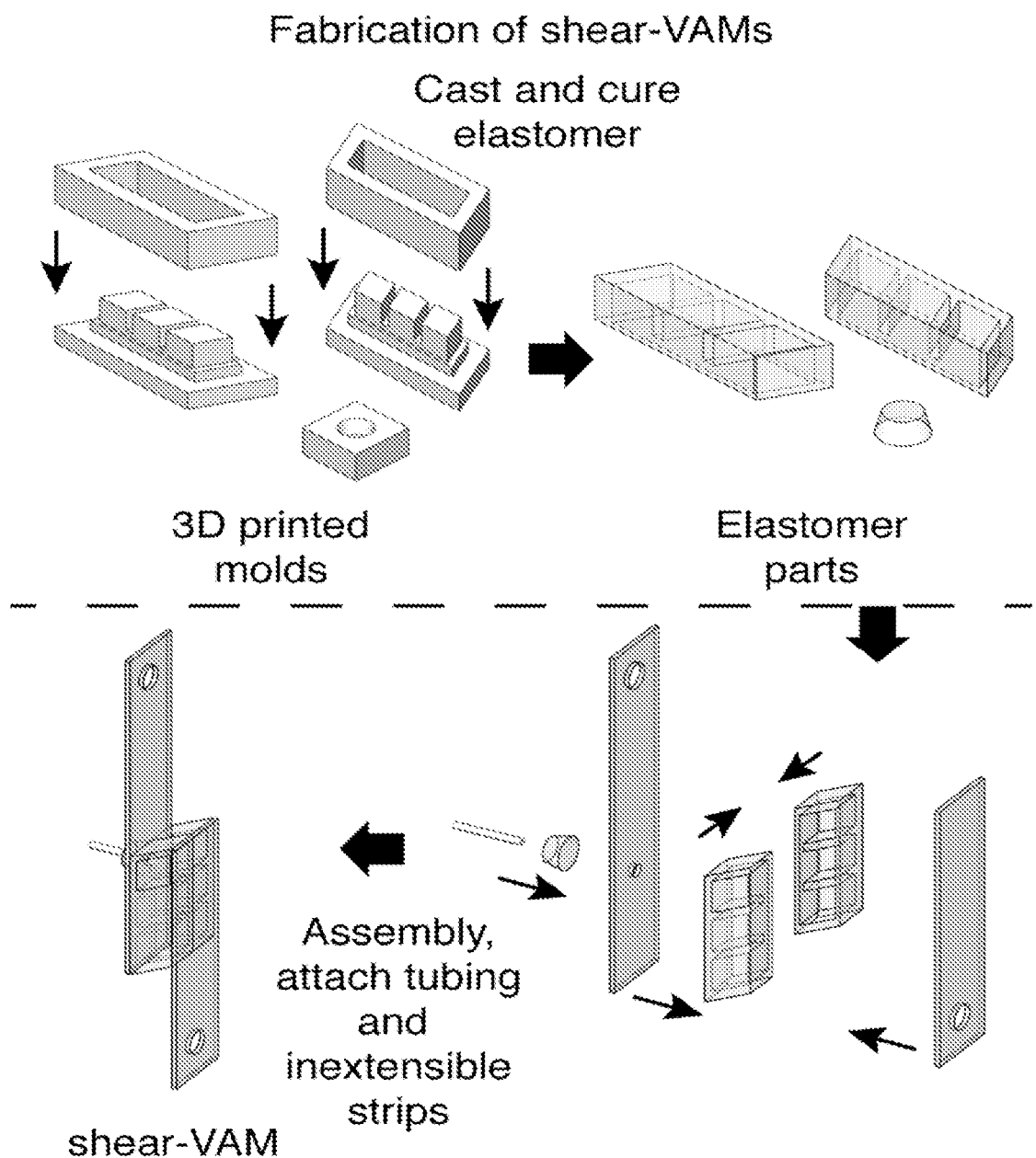
FIG. 5 illustrates the fabrication of shear-VAMs (also referred to as PIVAs), according to one or more embodiments described herein.

The elastomeric parts of shear-VAMs were created by replica molding (FIG. 5). We designed the molds using computer-aided design (CAD) (Solidworks) and fabricated them with acrylonitrile butadiene styrene (ABS) plastic using a 3D printer (StrataSys Fortus 250mc). Curing a silicone-based elastomer (Ecoflex 00-30, dragon skin 10 slow, or Elastosil M4601) against the molds at room temperature (4 hours for Ecoflex 00-30 and 6 hours for dragon skin 10 slow and Elastosil M4601) produced two halves of the shear-VAMs. These two halves were aligned and bonded together by applying uncured elastomer at their interface, prior to curing once again at room temperature for the same amount of time.

The inextensible strips were fabricated by placing pieces of nylon mesh on top of an acrylic plastic board, then pouring the corresponding elastomer over the mesh. A wooden stick was used to smooth the top surface of the elastomer. The composite strip is then formed after curing the elastomer in a 60° C. oven for 15 min. Two holes 6-mm in diameter are punched at the end of each strip for fixation purpose. Another smaller 3.5-mm diameter hole was punched on one of the two strips on a shear-VAM so that tubing could go through and transduce pneumatic pressure. The body of shear-VAM and the two strips were assembled by applying the same elastomer that they were made of as glue, and curing them at room temperature for 6 hours.

A conically-shaped piece of the elastomer was bonded to the side of the actuator to provide additional material that allowed tubing (Intramedic polyethylene tubing, ID 0.76 mm) to be securely attached to the structure. The conical piece was first pierced by a cannula. The tubing was fed through the cannula, which was then removed to leave the tubing embedded in the shear-VAM. The tubing was secured by elastic deformation of the elastomer, which, as the tubing displaced some of its volume, reacted by applying pressure to close the hole surrounding the tubing.

Why the Young's Modulus E of the Elastomeric Material Used to Fabricate a Shear-VAM is Proportional to is Maximum Force of Actuation $F_{max}$ A similar analysis was described in our paper on linear-VAMs. We have adapted the analysis here. Consider the body of the shear-VAM. Since the inextensible strips are not under substantial deformation during actuation, the two side surfaces of the shear-VAM that touch the inextensible strip can be considered to be each in a fixed boundary condition relative to itself. The two surfaces are, however, not fixed relative to each other. Due to the C2 symmetry of the shear-VAM, the two surfaces must move parallel to each other during actuation, and a shear stress is applied during this actuation. Let $\tau$ be the shear stress due to the hanging weight—that is, the load F divided by the lateral-area of the undeformed actuator A. And let s be the shear strain between the two surfaces—that is, the relative movement of the two strips $\Delta h$ divided by the length of the actuator L (Equation S1). We regard an actuator as a thermodynamic system of two independent variables that can independently change the state of the actuator—the difference of pressure $\Delta P$ and the loading stress $\tau$. To a good approximation, the elastomer is incompressible. Hence the state of the actuator depends on difference of pressure $\Delta P$, but not on the absolute pressures inside and outside the actuator. Since the experiment is insensitive to small change in temperature, we do not list temperature as a variable. Using the neo-Hookean model, we may obtain Equation S2 on the basis of dimensional considerations:

$$s = \Delta h/L \quad (S1)$$

$$s = g(\Delta P/E, \tau/E), \quad (S2)$$

where g is a function of two variables and E is the Young's modulus of the elastomeric material.

If we make two actuators with indistinguishable geometric features, but of materials with different Young's moduli, we can plots as a function of $\Delta P/E$ and $\tau/E$. The two surfaces will fall on top of each other.

Notice that according to Equation S2, if one increases E, $\Delta P$, and $\tau$ by a common factor k, one obtains the same strain s. Assuming E, $\Delta P$, and $\tau$ are increased to E'=kE, $\Delta P'$=k$\Delta P$, and $\tau'$=k$\tau$, we have relationship S3, where if Equation S2 describes a shear-VAM made of an elastomer of modulus E then Equation S4 must describe a shear-VAM of indistinguishable geometry, but made of an elastomer of modulus E'.

$$\tau/E = \tau'/E' \quad (S3)$$

$$s = g(\Delta P'/E', \tau'/E'), \quad (S4)$$

We note that a shear-VAM of modulus E can lift weight F=$\tau$A only if the absolute value of s($\Delta P$) monotonically increases with $\Delta P$; note also that Equation S2 and S4 as a function of $\Delta P$ must be simultaneously monotonically increasing, if one of them is so. Therefore a shear-VAM of modulus E can lift weight F=$\tau$A if and only if a shear-VAM of modulus E' can lift weight F'=$\tau$'A. In other words, the Young's modulus E of the elastomeric material used to fabricate a shear-VAM is proportional to the maximum load it can lift.

Measurement of Thermodynamic Efficiency

Figure 12A:
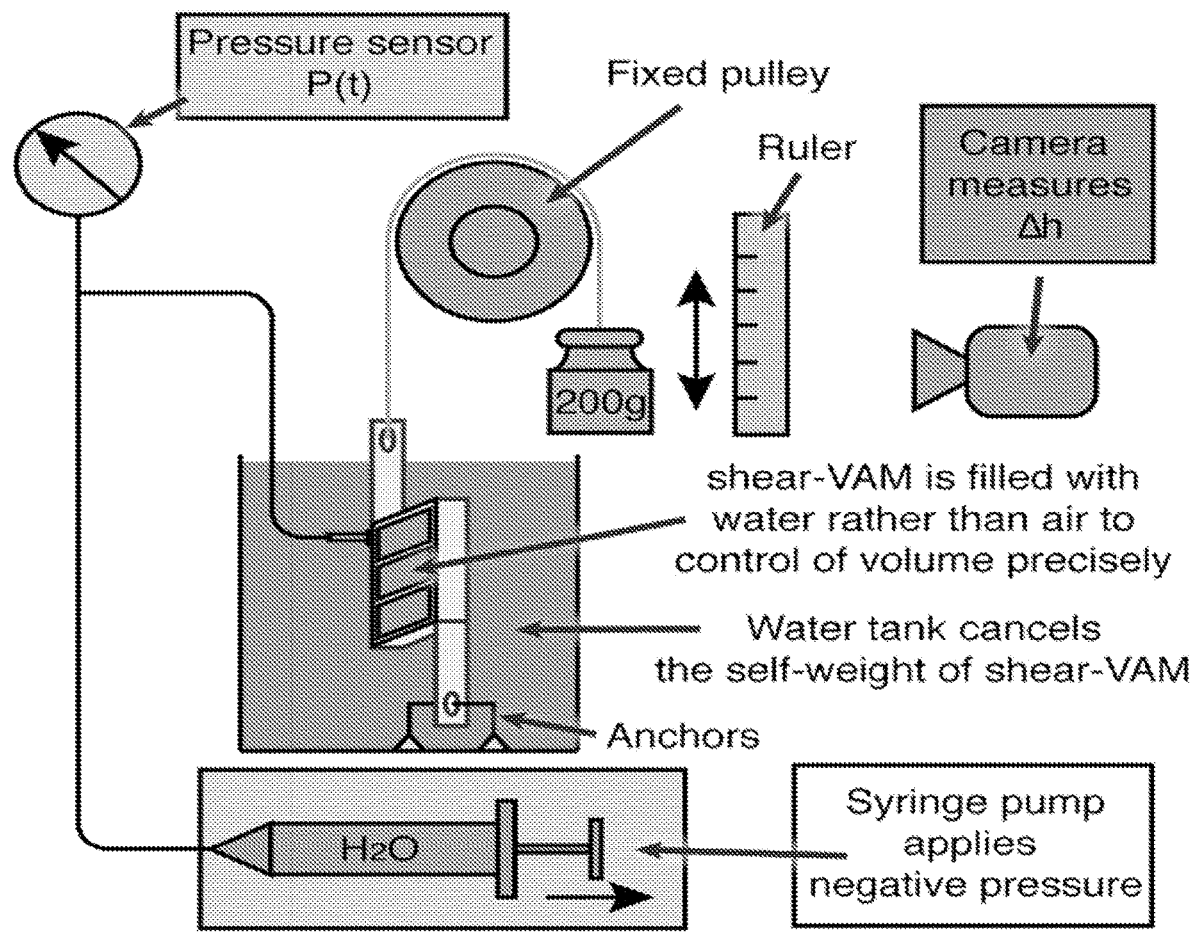
FIGS. 12A-12B show the Experiment used to determine the thermodynamic efficiency of operation of a shear-VAM.
Figure 12B:
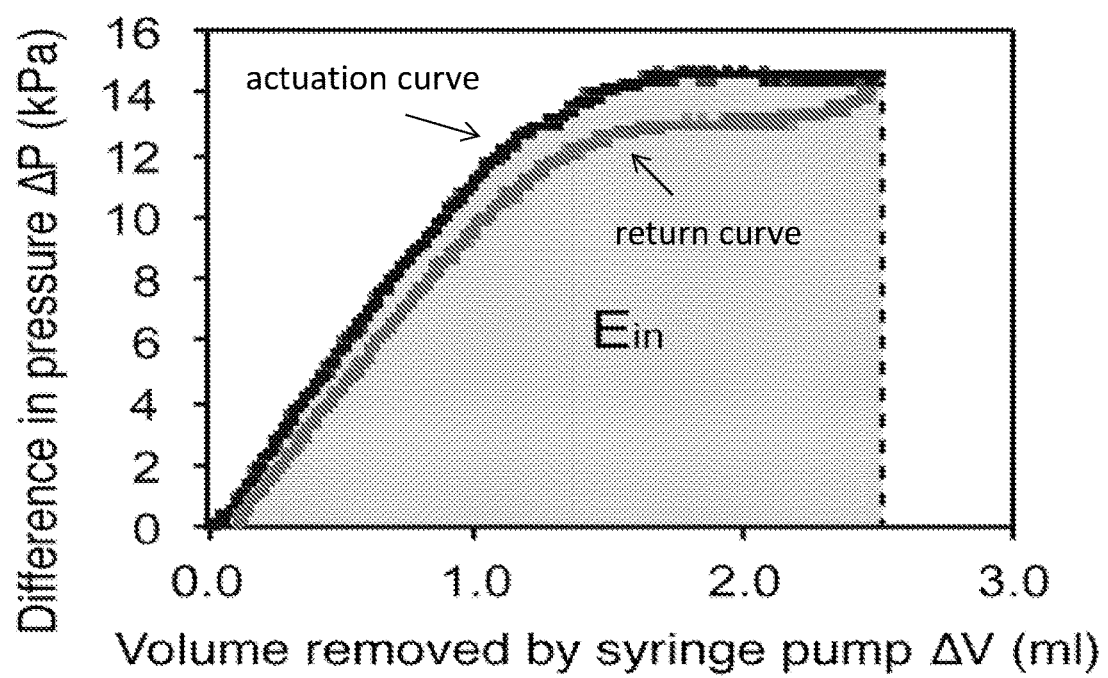

We generated the pressure-volume hysteresis curves by pumping water (an incompressible fluid) in and out of the shear-VAMs. The actuator was fully submerged in a 1-gallon container of water. The hydraulic actuation, and measurement of volume was performed with a syringe pump (Harvard Apparatus, PHD 2000), and the pressure measurement was performed with a pressure sensor (Transducers Direct, TDH31) connected to the syringe pump and the pressure transfer line (FIGS. 12A-12B). We fixated the actuator in a position that was submerged fully in water. We filled the actuators with water by submerging them in the container of water and deflating them several times until bubbles no longer emerged.

Within each test, we switched from deflation to inflation when the actuator had achieved approximately complete contraction (about 3 mL change in volume). We chose the rate of deflation and inflation to be 1 mL/min, which was sufficiently slow to achieve quasistatic conditions. We repeated the deflation-inflation cycle seven times.

The fluid used for inflation/deflation (water) is effectively incompressible that we could equate the volume decrease/increase of fluid in the syringe to that of the increase/decrease in the volume of the channels in the shear-VAMs. The shear-VAMs required removal of $V_0$=2 mL of water to achieve an actuation distance of $\Delta h$=~4.7 mm, while lifting a 200 g test weight, and while the applied differential pressure ramped up from 0 kPa to 15 kPa. We calculated the thermodynamic efficiency $\eta$ by dividing "energy out" $E_{out}$ by "energy in" $E_{in}$ (Equation S5). $E_{out}$ was obtained by calculating the potential energy gain of lifting the weight (m=200 g was the weight we used, and g is the acceleration due to gravity) (Equation S6). $E_{in}$ was obtained by integrating the differential pressure with respect to the change in volume (Equation S7). This value is represented by the area under the P-V curve (FIG. 12B).

$$\eta = E_{out}/E_{in}. \quad (S5)$$

$$E_{out} = mg\Delta h. \quad (S6)$$

$$E_{in} = \int_0^{V_0} P(V) dV. \quad (S7)$$

Over a total of six runs, we obtained an efficiency of $\eta$=35%±1%. Note that the loss of energy due to hysteresis was small compared to the work done by the syringe pump during actuation (FIG. 12B). The loss of efficiency was mainly due to the storage of elastic energy in the elastomer, with a small contribution from hysteresis.

Approximate Theoretical Derivation of the Force of Actuation F

Due to conservation of energy, the generation of a higher force of actuation F of shear-VAM (or of any other pneumatic actuators) requires the supply of a higher difference of pressure $\Delta P$. Although $\Delta P$ is limited to 1 atm under atmospheric pressure, we will show that the force of actuation F of shear-VAMs increases linearly to the "lateral-area" of the strip A under fixed $\Delta P$, limited only by the tensile strength of the strips. We will show that, unique to shear-VAM, the effective cross-sectional area of a shear-VAM does not necessarily increase as we increase A, allowing the shear-VAM to generate a mechanical advantage.

We can derive (approximately) the force of actuation Fa shear-VAM produces for a given difference of pressure $\Delta P$ (that is less than the critical difference of pressure of a shear-VAM $\Delta P_{crit}$) through an analysis of virtual work. When a difference of pressure $\Delta P$ is applied, the volume of the void chambers decreases, and the two strips move towards each other. Assume an infinitesimal reduction of angle $\alpha$ to $\alpha-\delta\alpha$ (in radian), while the "lateral-area" A moves under force $\Delta P \times A$, and the shear-VAM reduces its volume from $A \times a \times \sin(\alpha)$ to $A \times a \times \sin(\alpha-\delta\alpha)$. The pneumatics virtual work (pressure-volume work) done to the system is:

$$\delta W_{in} = \Delta P \times \delta V = \Delta P \times A \times (a \times \sin(\alpha) - a \times \sin(\alpha - \delta\alpha)) \quad (S8)$$
$$= \Delta P \times A \times a \times \cos(\alpha) \times \delta\alpha$$

where $\delta V$ is the change of overall volume of the elastomeric part of shear-VAM. Since the elastomer is incompressible, $\delta V$ is also equal to the volume of air pumped out of the void chambers of the shear-VAM. In the meantime, the shear-VAM exerts force F over a distance of $\delta h = (a \times \cos(\alpha-\delta\alpha) - a \times \cos(\alpha))$. The virtual work output (force-distance work) by the system to lift the load is:

$$\delta W_{out} = F \times \delta h = F \times (a \times \cos(\alpha-\delta\alpha) - a \times \cos(\alpha)) \quad (S9)$$
$$= F \times a \times \sin(\alpha) \times \delta\alpha$$

Dividing Equation S9 by Equation S8, we obtain:

$$\eta(\alpha) = \delta W_{out}/\delta W_{in} = F \times \tan(\alpha)/(\Delta P \times A) \quad (S10)$$

where $\eta(\alpha)$ is the efficiency of the shear-VAM near angle $\alpha$, defined as the ratio between work out $\delta W_{out}$ and work in $\delta W_{in}$ (Equation S10). Since we know $\delta W_{in} = \delta W_{out} + \delta W_{lost}$ where $\delta W_{lost}$ is the elastic and inelastic energy lost in compressing the elastomers, we know $\eta(\alpha) < 1$. Equivalently, Equation S10 can be written as a formula for the force of actuation F $$F = \eta(\alpha) \times \Delta P \times A/\tan(\alpha) \quad (S11)$$

The efficiency $\eta(\alpha)$ comes primarily from the elastic loss in collapsing the chambers, and should be, in principle, constant (for the same angle $\alpha$) as long as the beam length a and the beam spacing (10 mm in this design) are fixed. This efficiency $\eta(\alpha)$ is approximately equal to the thermodynamic efficiency of the shear-VAM $\eta$. Using the data plotted in FIG. 9*a*), the efficiency $\eta(\alpha)$ in two shear-VAMs of different length L=62 mm. 32 mm can be calculated using Equation S10: the efficiencies are about the same for the two different lengths L, at ~40% (at $\Delta P \approx 2$ kPa, $\alpha \approx 45°$), and they are similar to the total thermodynamic efficiency of the shear-VAM (~35%).

In this derivation, we assumed the contribution of out-of-plane deformation of the inextensible strips to $\Delta h$ is negligible—this assumption is especially true if the strips are made of materials with high stiffness. For more flexible strips, the $\Delta h$ will be larger than our estimation due to tilting of the elastomeric body at un-actuated state (FIG. 4B shows an example of this tilting), resulting in an under-estimation of $\delta h$. We also assume that the deformation of the elastomeric membranes negligible. This assumption results in an over-estimation of change in volume $\delta V$ as a function of angle $\alpha$. Overall, these assumptions result in an overestimation of F, since:

$$F \times \delta h = \eta \times \Delta P \times \delta V \quad (S12)$$

This estimation, however, doesn't change the qualitative behavior of F. Thus we can still use Equation S11 to study the scaling properties of F, which is the purpose of this derivation.

Experimental Procedure for Measuring the Relationship Between the Force of Actuation F and the Difference of Pressure $\Delta P$ FIG. 8 shows a schematic diagram for the testing setup that measures relationship between the force of actuation F of shear-VAMs and the difference of pressure $\Delta P$ applied across the inside and outside of the shear-VAMs. The bottom end of each shear-VAM is tied to a weight placed on a scale to measure the force of actuation of the shear-VAM. The forces did not exceed the weight and thus, the weight did not lift off the scale. The scale together with the weight acts as a strain gauge to measure the force of actuation F of the shear-VAMs.

We generated the difference of pressure $\Delta P$ (i.e. a partial vacuum) by pumping air out of the actuator with a syringe connected to a syringe pump (Harvard Apparatus, PHD 2000). The pressure measurement was performed with a pressure sensor (Honeywell ASDX005D44R) connected to the syringe pump and the pressure transfer line (FIG. 8). The voltage signal from the pressure sensor is received through a DAQ (NI USB-6210) and read with National Instruments™ LabVIEW. We slowly extracted air using the syringe pump at a rate of 2 mL/min and recorded the force readings at predetermined values of pressure. We repeated the deflation-inflation cycle seven times to obtain error bars for FIG. 9D.

"Shear-VAMs" Actuated with Positive Pressure

Figure 13:
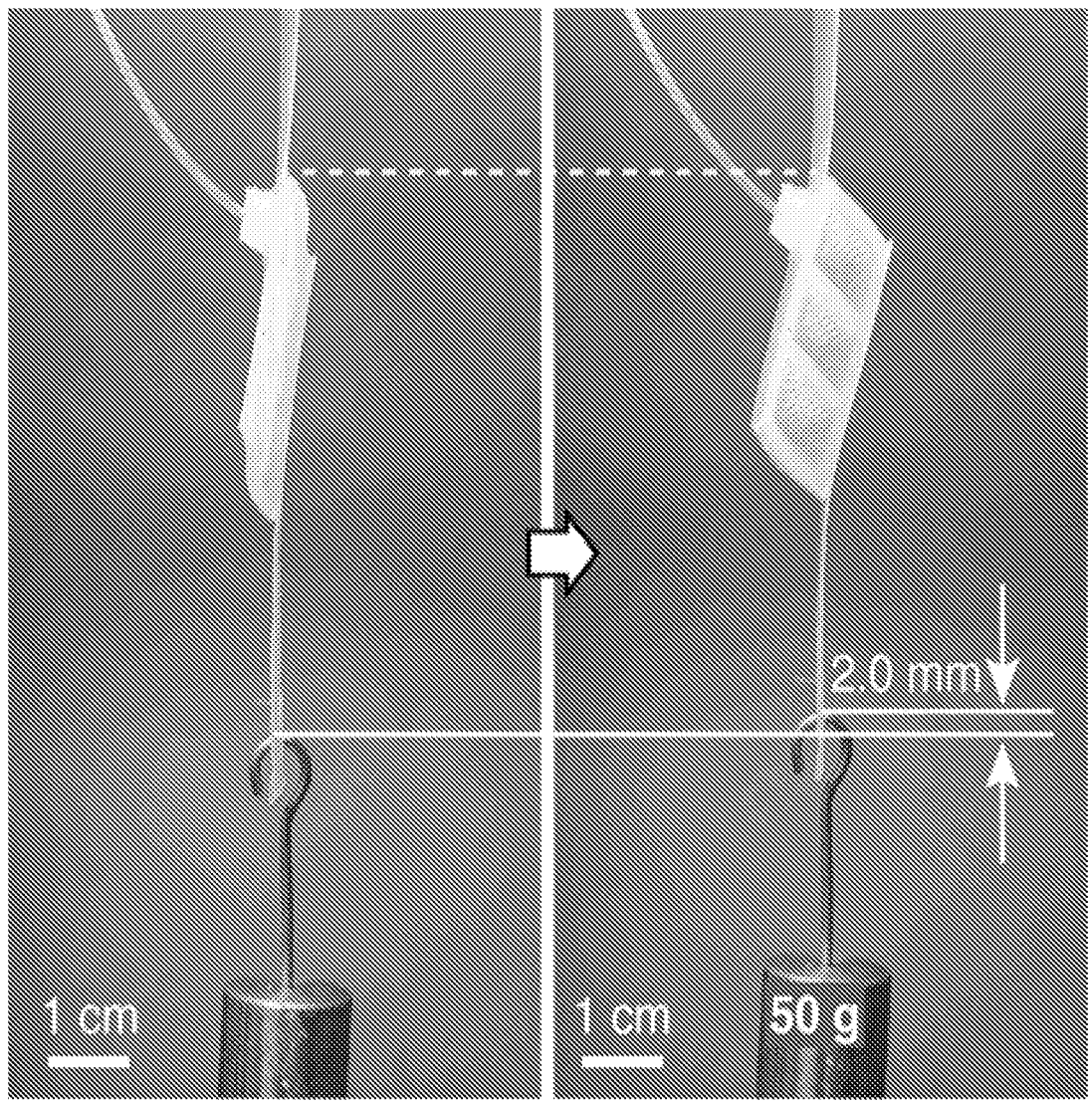
FIG. 13 shows a variant of shear-VAM made of Ecoflex (E=43 kPa) with four beams and length L=32 mm that is driven by positive pressure lifts a 50-g weight. The distance of actuation $\Delta$h is less than that of a normal shear-VAM operated by vacuum.

We can vary the design of a shear-VAM to generate an actuation stress by inflating the structure rather than deflating it. FIG. 13 shows a variant of shear-VAM made of Ecoflex (E=43 kPa) with four beams that is driven by positive pressure to lift a 50 g-weight. This actuator is made based on a shear-VAM but the elastomeric body is glued in the opposite direction to the strips so that the angle between the beams and the strips $\alpha < 90°$ is now $\alpha' = 180° - \alpha > 90° < 90°$. This configuration generates a smaller distance of actuation $\Delta h$ than a normal shear-VAM.

The foregoing and other features and advantages of various aspects of the invention(s) will be apparent from the following more particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

We claim:

1. A shear force actuator comprising:
   two first structural components made of a flexible but inextensible material and disposed along a first axis, wherein the two first structural components deviate from being parallel by less than 35°;
   a plurality of second structural components disposed between and bridging the two first structural components, wherein the plurality of second structural components deviate from being parallel by less than 35°;
   a plurality of joint sections each joining the plurality of second structural components with the first structural components at an oblique angle of between 0 and 90 degrees to define a plurality of cells, each capable of being connected with a fluid inflation or deflation source;
   a surface covering the remaining surfaces of the cells in a fluid-tight manner; wherein
   at least one of the joint sections, the first structural components, and the second structural components is elastic so that the cell collapses upon removal of fluid from the cell to generate a linear force along the first axis.

2. The shear force actuator of claim 1, wherein the joint section is elastic.

3. The shear force actuator of claim 1, wherein the second structural components are elastic.

4. The shear force actuator of claim 1, wherein the two first structural components are not elastic.

5. The shear force actuator of claim 1, wherein the first structural components and/or the second structural components are made of non-deformable hard materials and/or the joint section is made of deformable soft material or is a hard hinge.

6. The shear force actuator of claim 5, wherein the hard hinge is made of a hard material selected from the group consisting of metal, plastic, glass, wood, and stone.

7. The shear force actuator of claim 1, wherein the joint section is a hinge, a pivot, or other rotational coupling mechanism coupling the first and second components.

8. The shear force actuator of claim 1, wherein the oblique angle is 30, 40, 45, 60, 65, 70, or 75 degrees.

9. The shear force actuator of claim 1, comprising more than 2, 5, 20, 50, or 100 second structural components.

10. The shear force actuator of claim 1, wherein the plurality of cells are configured to be connected to each other and configured for connection with the same fluid inflation or deflation source, but are otherwise isolated from the atmosphere.

11. The shear force actuator of claim 1, wherein the first axis is horizontal or vertical.

12. The shear force actuator of claim 1, wherein the surface is elastomeric or hard.

13. The shear force actuator of claim 1, wherein the surface is hard and at least one of the first and second structural components are slidable along the surface without breaking the fluidic seal.

14. The shear force actuator of claim 1, wherein the surface is planar.

15. The shear force actuator of claim 1, wherein the contact between the surface and the first and second structural components are lubricated with a lubricant.

16. The shear force actuator of claim 1, wherein the cell is configured to collapse upon the removal of the fluid and return to its original position when the deflated cell is re-inflated.

17. The shear force actuator of claim 1, wherein the first and/or second structural components have high aspect ratio.

18. The shear force actuator of claim 1, wherein the joint section and/or the second structural components are made from an elastic polymer.

19. The shear force actuator of claim 1, wherein the fluid is a gas or liquid.

20. The shear force actuator of claim 1, wherein the fluid is air.

21. The shear force actuator of claim 1, wherein the cell is connected to a gas inflation/deflation source via a fluid chamber.

22. The shear force actuator of claim 1, wherein the cell is in the form of a rod, slit, sphere, cube, hexahedron, or cylinder.

23. The shear force actuator of claim 1, wherein the second structural components or its cross-sections are in the form of a pillar, a lever, or beam.

24. The shear force actuator of claim 1, wherein the fluid inflation or deflation source is a gas pump, a gas vacuum, or a gas pump and vacuum.

25. The shear force actuator of claim 1, further comprising a hard and/or soft body portion.

26. An actuator comprising a plurality of shear force actuators each according to claim 1.

27. A method of actuation, comprising:
   providing the shear force actuator of claim 1; and
   deflating or inflating the cells to cause the cells to collapse or expand, respectively, to generate a linear force.

28. A shear force actuator comprising:
   two first structural components disposed along a first axis;
   a plurality of second structural components disposed between and bridging the two first structural components, wherein the second components deviate from being parallel by less than 35°;
   a plurality of joint sections each joining the plurality of second structural components with the first structural components at an oblique angle of between 0 and 90 degrees to define a plurality of cells, each capable of being connected with a fluid inflation or deflation source;
   a surface covering the remaining surfaces of the cells in a fluid-tight manner; wherein
   at least one of the joint sections, the first structural components, and the second structural components is elastic so that the cell collapses upon removal of fluid from the cell to generate a linear force along the first axis, and
   wherein the surface is hard and at least one of the first and second structural components are slidable along the surface without breaking the fluidic seal.

29. A shear force actuator comprising:
   two first structural components disposed along a first axis;
   a plurality of second structural components disposed between and bridging the two first structural components, wherein the second components deviate from being parallel by less than 35°;
   a plurality of joint sections each joining the plurality of second structural components with the first structural components at an oblique angle of between 0 and 90 degrees to define a plurality of cells, each capable of being connected with a fluid inflation or deflation source;

a surface covering the remaining surfaces of the cells in a fluid-tight manner; wherein at least one of the joint sections, the first structural components, and the second structural components is elastic so that the cell collapses upon removal of fluid from the cell to generate a linear force along the first axis, and wherein the contact between the surface and the first and second structural components are lubricated with a lubricant.

* * * * *